United States Patent [19]
Torczynski et al.

[11] Patent Number: 5,589,579
[45] Date of Patent: Dec. 31, 1996

[54] GENE SEQUENCE AND PROBE FOR A MARKER OF NON-SMALL CELL LUNG CARINOMA

[75] Inventors: Richard M. Torczynski; Arthur P. Bollon, both of Dallas, Tex.

[73] Assignee: Cytoclonal Pharmaceutics, Inc., Dallas, Tex.

[21] Appl. No.: 276,919

[22] Filed: Jul. 19, 1994

[51] Int. Cl.$^6$ ............................... C12Q 1/68; C07H 21/02
[52] U.S. Cl. ............................. 536/23.1; 435/6; 536/23.5
[58] Field of Search ................................ 435/6; 536/23.2, 536/23.5

[56] References Cited

U.S. PATENT DOCUMENTS

| | | | |
|---|---|---|---|
| 4,816,402 | 3/1989 | Rosen et al. | 435/240.27 |
| 4,990,454 | 2/1991 | Yachi et al. | 435/240.27 |
| 5,134,075 | 7/1992 | Hellstrom et al. | 530/387.3 |
| 5,185,432 | 2/1993 | Hellstrom et al. | 530/388.8 |
| 5,200,508 | 4/1993 | Nilaver et al. | 530/350 |

OTHER PUBLICATIONS

Mori, et al., "The significance of carbonic anyhdrase expression in human colorectal cancer," *Gastroenterology* 105:820–826 (1993). Abstract only.

Skonier, et al., "cDNA cloning and sequence analysis of βig–h3, a novel gene induced in a human adenocarcinoma cell line after treatment with transforming growth factor–β," *DNA Cell Biology* 11:511–522 (1992).

Mason and Housley, J. Biol. Chem. 268(24): pp. 21501–21504 (1993).

Anastasi, et al., "Direct correlation of cytogenetic findings with cell morphology using in situ hybridization: an analysis of suspicious cells in bone morrow specimens of two patients completing therapy for acute lymphoblastic leukemia," *Blood* 77:2456–2462 (1991).

Altschul, et al., "Basic local alignment search tool," *J. Molecular Biol* 215:403–410 (1990).

Birrer, et al., "Application of molecular genetics to the early diagnosis and screening of lung cancer," *Cancer Research (supplement)* 52:2658s–2664s (1992).

Boring, et al., "Cancer statistics, 1993," *CA Cancer J Clin* 43:7–26 (1993).

Chirgwin, et al., "Isolation of biologically active ribonucleic acid from sources enriched in ribonuclease," *Biochem* 18:5294–5299 (1979).

Diez, et al., "Prognostic significance of serum CA 125 antigen assay in patients with non–small cell lung cancer," *Cancer* 73:1368–1376 (1994).

Flehinger, et al., "The effect of surgical treatment on survival from lung cancer: implications for screening," *Chest* 101:1013–1018 (1992).

Gray, J W and Pinkel, D, "Molecular cytogenetics in human cancer diagnosis," *Cancer (supplement)* 69:1536–1542 (1992).

(List continued on next page.)

Primary Examiner—W. Gary Jones
Assistant Examiner—Ethan Whisenant
Attorney, Agent, or Firm—Richards, Medlock & Andrews

[57] ABSTRACT

The present invention discloses an isolated and purified nucleic acid sequence and corresponding amino acid sequence to a novel protein specific for human lung cancer cells. This gene is expressed at a much higher level in these cells than in normal lung, other normal tissues and other tumor cell lines tested. Also disclosed are two additional recombinant forms of this gene and protein, in the first case a membrane spanning region is removed and in the second case an amino acid is changed by in vitro mutagenesis. Also disclosed are nucleic acid probes for the detection of lung cancer cells from tissue biopsy and body fluids such as serum, sputum and bronchial washings. A method for expressing the antigen in a host cell and its subsequent use as an immunogen in antibody production for test applications is described. An ELISA test to measure shed antigen present in patient samples as well as an enzyme test to measure activity in specimens also is described.

15 Claims, 1 Drawing Sheet

```
HCAI      ASPDWGYDDKNGPE-QWSKLYPIA-NGN----NQSPVDIKTSETKHDTSLKPISVS-YNPATAKE--IIWVGHSFHVNFEDNDN
HCAII     -SHHWGYGKHNGPE-HWHKDFPIA-KGE----RQSPVDIDTHTAKYDPSLKPLSVS-YDQATSLR--ILWNGHAFNVEFDDSQD
HCAIII    -AXEWGYASHNGPD-HWHELFPNA-KGE----NQSPVELHTKDIRHDPSLQPWSVS-YDGGSAKT--ILWNGKTCRVVFDDTYD
HCAIV     AESHWCYEVQAESS-NYPCLVPVKWGGNCQKDRQSPINIVTTKAKVDKKLGRFFFSGYDKKQTWT--VQMNGHSVMMLLEN--K
HCAVI     QHVSDWTYSEGALDEAHWPQHYPAC-GGQ----RQSPINLQRTKVRYNPSLKGLNMTGYETQAGEFP-MVMNGHTVQIGLPSTMR
HCAVII    GHHGWGYGQ-DDGPSHWHKLYPIA-QG----DRQSPINIISSQAVYSPSLQPLELS-YEACMSLS--ITNNGHSVQVDFNDSDD
HCAV      --CAWQTSNNTLHP-LWTVPVSVP-GGT----RQSPINIQWRDSVYDPQLKPLRVS-YEAASCLY--IWWTGYLFQVEFDDATE
HCAVIII   --SKWTYFGPDGEN-SWSKKYPSC-GGL----LQSPIDLHSDILQYDASLTPLEFQGYNLSANKQFLLTWNGHSVKLNLP-S-D

HCAI      RSVLKGGPFSDSYRLFQFHFHWG--STNEHGSSHTVDGVKYSAELHVAH-WNSAKYSSLAEAASKADGLAVIGVLM--KVG-EA
HCAII     KAVLKGGPLDGTYRLIQFHFHWG--SLDGQGSSHTVDKKKYAAELHLVH-WNT-KYGDFGKAVQQPDGLAVLGIFL--KVG-SA
HCAIII    RSMLRGGPLPGPYTRLRQFHLHWG--SSDDHGSSHTVDGVKYAABLHLVH-WNP-KYNTFKEALKQRDGIAVIGIFL--KIG-HE
HCAIV     ASISGGG--LPAPYQAKQLHLHWS--DLPYKGSSHSLDGEHFAMEMKTVHEKEKGTSRNVKEAQDPEDEIAVLAFLV--EAGTQV
HCAVI     MTVA-DG---IVYIAQQMHFHWGGASSEISGSSHTVDGIRHVIEIHIVH-YNS-KYKTYDIAQDAPDGLAVLAAFVEVKNY-PE
HCAVII    RTVVTGGPLEGPYRLKQFHFHWG--KKHDVGSSHTVDGKSFPSELHLVH-WNAKKYSTFGEAASAPDGLAVVGVFL--ETG-DE
HCAV      ASGISGGPLENHYRLKQFHFHWG--AVNEGGSSHTVDGHAYPAELHLVH-WNSVKYQNYKEAVVGENGLAVIGVFL--KLG-AH
HCAVIII   --MHIQG-LQSRYSATQLHLHWG-NPNDPHGSSHTVSGQHFAAELHIVH-YNSDLYPDASTASNKSEGLAVLAVLI--EMG-SF

HCAI      NPKLQKVLDALQAIKTKGKRAPFTNFDPSTLLPSSL---DFWTYPGSLTHPPLYESVTWIICKESISVSSEQLAQF-RSLLSNV
HCAII     KPGLQKVVDVLDSIKTKGKSADFTNFDPRGLLPESL---DYWTYPGSLTTPPLLECVTWIVLKEPISVSSEQVLKF-RKLNFNG
HCAIII    NGEFQIFLDALDKIKTKGKEAPFTKFDPSCLFPACR---DYWTYQGSFTTPPCEECIVWLLLKEPMTVSSDQMAKL-RSLLSSA
HCAIV     NEGFQPLVEALSNIPKPEMSTTMAESSLLDLLPKEEKLRHYFRYLGSLTTPTCDEKVVWTVFREPIQLHREQILAFSQKL--YY
HCAVI     NTYYSNFISHLANIKYPGQRTTLTGLDVQDMLPRNLQ--HYYTYHGSLTTPPCTENVHWFVLADFVKLSRTQVWKLENSLLDHR
HCAVII    HPSMNRLTDALYMVRFKGTKAQFSCFNPKCLLPAS---RHYWTYPGSLTTPPLSESVTWIVLREPICISERQMGKF-RSLLFTS
HCAV      HQTLQRLVDILPEIKHKDARAAMRPFDPSTLLPTCW---DYWTYAGSLTTPPLTESVTWIIQKEPVEVAPSQLSAF-RTLLFSA
HCAVIII   NPSYDKIFSHLQHVKYKGQEAFVPGFNIEELLPERT--AEYYRYRGSLTTPPCNPTVLWTVFRNPVQISQFQLLALETALYCTH

HCAI      EGDNAVPMQHWN-RPTQPLKGRTVRASF
HCAII     EGEPEELMVDWW-RPAQPLKNRQIKASFK
HCAIII    ENEPPVPLVSWW-RPPQPINNRVVRASFK
HCAIV     DKEQTVSMKDNV-RPLQQLGQRTVIKSGAPGRPLPWALPALLGPMLACLLAGFLR
HCAVI     NKTIH------NDYRRTQPLKHRVVE-SNFPNQEYTLGSEFQFYLHKIEEILDYLRRALN
HCAVII    EDDERI-HMVWNFRFPQPLKGRVVKASFRA
HCAV      LGEEEK-MMVNNYRPLQPLMNRKVWASFQATNEGTRS
HCAVIII   MDDPSPREMINNFRQVQKFDERLVYTSFSQVQVCTAAGLSLGIILSIALAGILGICIVVVVSIWLFRRKSIKKGDNKGVIYKPA

HCAVIII   TKMETEAHA*
```

OTHER PUBLICATIONS

Hasegawa, et al., "Nonspecific crossreacting antigen (NCA) is a major member of the carcinoembryonic antigen (CEA)–related gene family expressed in lung cancer," *British J Cancer* 67:58–65 (1993).

von Heijne, G., "A new method for predicting signal sequence cleavage sites," *Nucleic Acid Research* 14:4683–4690 (1986).

Kern, et al., "p185$^{neu}$ Expression in human lung adenocarcinomas predicts shortened survival," *Cancer Research* 50:5184–5191 (1990).

Kim, et al., "Interphase cytogenetics in paraffin sections of lung tumors by non–isotopic in situ hybridization," *Am J Path* 142:307–317 (1993).

Kunkel, T. A., "Rapid and efficient site–specific mutagenesis without phenotypic selection," *Proc Natl Acad Sci USA* 82:488–492 (1985).

Margolis, et al., "Serum tumor markers in non–small cell lung cancer," *Cancer* 73:605–609 (1994).

Melamed, et al., "Screening for early lung cancer: results of the Memorial Sloan–Kettering study in New York," *Chest* 86:44–53 (1984).

Mitsudomi, et al., "p53 gene mutations in non–small–cell lung cancer cell lines and their correlation with the presence of ras mutations and clinical features," *Oncogene* 7:171–180 (1992).

Mulshine, et al., "Section 22.5 Applications of monoclonal antibodies in the treatment of solid tumors," *Biologic Therapy of Cancer,* V T DeVita, S. Hellman, S A Rosenberg (ed), J B Lippencott Co., New York, pp. 563–588 (1991).

Parkin, et al., "Estimates of the worldwide incidence of eighteen major cancers in 1985," *Int J Cancer 54:594–606 (1993).*

Radosevich, et al., "Monoclonal antibody assays for lung cancer," *Cancer Diagnosis In Vitro Using Monoclonal Antibodies,* H. Kupchik (ed.), Marcel Dekker, Inc., New York, pp. 101–121 (1988).

Schepart, B S and Margolis, M L, "Monoclonal antibody–mediated detection of lung cancer antigens in serum," *Am Rev Respir Dis* 138:1434–1438 (1988).

Scott, et al., "Early lung cancer detection using monoclonal antibodies," *Lung Cancer,* J A Roth, J D Cox, and W K Hong (eds), Blackwell Scientific Publications, Boston, pp. 310–323 (1993).

Smith, D B and Johnson, K S, "Single–step purification of polypeptides expressed in *Escherichia coli* as fusions with glutathione S–transferase," *Gene* 67:31–40 (1988).

Souhami, et al., "Antigens of lung cancer: results of the Second International Workshop on Lung Cancer Antigens," *J Natl Cancer Institute* 83:609–612 (1991).

Strnad, et al., "Molecular cloning and characterization of a human adenocarcinoma/epithelial cell surface antigen complementary DNA," *Cancer Research* 49:314–317 (1989).

Tockma, et al., "Sensitive and specific monoclonal antibody recognition of human lung cancer antigen on preserved sputum cells: a new approach to early lung cancer detection," *J Clin Oncology* 6:1685–1693 (1988).

Anon, "Early lung cancer detection: summary and conclusions," *Am Rev Respir Dis* 130:565–570 (1984).

"The World Health Organization histological typing of lung tumours (second edition)," *Am J Clin Path* 77:123–136 (1982).

```
HCAI     ASPDWGYDDKNGPE-QWSKLYPIA-NGN-----NQSPVDIKTSETKHDTSLKPISVS-YNPATAKE--IINVGHSFHVNFEDNDN
HCAII    -SHHWGYGKHNGPE-HWHKDFPIA-KGE-----RQSPVDIDTHTAKYDPSLKPLSVS-YDQATSLR--ILNNGHAFNVEFDDSQD
HCAIII   -AKEWGYASHNGPD-HWHELFPNA-KGE-----NQSPVELHTKDIRHDPSLQPWSVS-YDGGSAKT--ILNNGKTCRVFDDTYD
HCAIV    AESHWCYEVQAESS-NYPCLVPVKWGGNCQKDRQSPINIVTTKAKVDKKLGRFFFSGYDKKQTWT--VQNNGHSVMMLLEN--K
HCAVI    QHVSDWTYSEGALDEAHWPQHYPAC-GGQ-----RQSPINLQRTKVRYNPSLKGLNMTGYETQAGEFP-MVNNGHTVQIGLPSTMR
HCAVII   GHHGWGYGQ-DDGPSHWHKLYPIA-QG------DRQSPINIISSQAVYSPSLQPLELS-YEACMSLS--ITNNGHSVQVDFNDSDD
HCAV     --CAWQTSNNTLHP-LWTVPVSVP-GGT-----RQSPINIQWRDSVVDPQLKPLRVS-YEAASCLY--IWNTGYLFQVEFDDATE
HCAVIII  ---SKWTYFGPDGEN-SWSKKYPSC-GGL-----LQSPIDLHSDILQYDASLTPLEFQGYNLSANKQFLLTNNGHSVKLNLP-S-D

HCAI     RSVLKGGPFSDSYRLFQFHFHWG---STNEHGSEHTVDGVKYSAELHVAH-WNSAKYSSLAEAASKADGLAVIGVLM--KVG-EA
HCAII    KAVLKGGPLDGTYRLIQFHFHWG---SLDGQGSEHTVDKKKYAAELHLVH-WNT-KYGDFGKAVQQPDGLAVLGIFL--KVG-SA
HCAIII   RSMLRGGPLPGPYRLRQFHFHWG---SSDDHGSEHTVDGVKYAAELHLVH-WNP-KYNTFKEALKQRDGIAVIGIFL--KIG-HE
HCAIV    ASISGGG-LPAPYQAKQLHLHWS---DLPYKGSEHSLDGEHFAMEMHIVHEKEKGTSRNVKEAQDPEDELAVLAFLV--EAGTQV
HCAVI    MTVA-DG---IVYIAQQMHFHWGGASSEISGSEHTVDGIRHVIEIHIVH-YNS-KYKTYDIAQDAPDGLAVLAAFVEVKNY-PE
HCAVII   RTVTGGPLEGPYRLKQFHFHWG---KKHDVGSEHTVDGKSFPSELHLVH-WNAKKYSTFGEAASAPDGLAVVGVFL--ETG-DE
HCAV     ASGISGGPLENHYRLKQFHFHWG---AVNEGGSEHTVDGHAYPAELHLVH-WNSVKYQNYKEAVVGENGLAVIGVFL--KLG-AH
HCAVIII  --MHIQG-LQSRYSATQLHLHWG-NPNDPHGSEHTVSGQHFAAELHIVH-YNSDLYPDASTASNKSEGLAVLAVLI--EMG-SF

HCAI     NPKLQKVLDALQAIKTKGKRAPFTNFDPSTLLPSSL----DFWTYPGSLTHPPLYESVTWIICKESISVSSEQLAQF-RSLLSNV
HCAII    KPGLQKVVDVLDSIKTKGKSADFTNFDPRGLLPESL----DYWTYPGSLTTPPLLECVTWIVLKEPISVSSEQVLKF-RKLNFNG
HCAIII   NGEFQIFLDALDKIKTKGKEAPFTKFDPSCLFPACR---DYWTYQGSFTTPPCEECIVWLLLKEPMTVSSDQMAKL-RSLLSSA
HCAIV    NEGFQPLVEALSNIPKPEMSTTMAESSLLDLLPKEEKLRHYFRYLGSLTTPTCDEKVVWTVFREPIQLHREQILAFSQKL--YY
HCAVI    NTYYSNFISHLANIKYPGQRTTLTGLDVQDMLPRNLQ--HYYTYHGSLTTPPCTENVHWFVLADFVKLSRTQVWKLENSLLDHR
HCAVII   HPSMNRLTDALYMVRFKGTKAQFSCFNPKCLLPAS----RHYWTYPGSLTTPPLSESVTWIVLREPICISERQMGKF-RSLLFTS
HCAV     HQTLQRLVDILPEIKHKDARAAMRPFDPSTLLPTCW----DYWTYAGSLTTPPLTESVTWIIQKEPVEVAPSQLSAF-RTLLFSA
HCAVIII  NPSYDKIFSHLQHVKYKGQEAFVPGFNIEELLPERT--AEYYRYRGSLTTPPCNPTVLWTVFRNPVQISQEQLLALETALYCTH

HCAI     EGDNAVPMQHNN--RPTQPLKGRTVRASF
HCAII    EGEPEELMVDNW--RPAQPLKNRQIKASFK
HCAIII   ENEPPVPLVSNW--RPPQPINNRVVRASFK
HCAIV    DKEQTVSMKDNV--RPLQQLGQRTVIKSGAPGRPLPWALPALLGPMLACLLAGFLR
HCAVI    NKTIH------NDYRRTQPLKHRVVE-SNFPNQEYTLGSEFQFYLHKIEEILDYLRRALN
HCAVII   EDDERI-HMVNNFRPPQPLKGRVVKASFRA
HCAV     LGEEEK-MVNNYRPLQPLMNRKVWASFQATNEGTRS
HCAVIII  MDDPSPREMINNFRQVQKFDERLVYTSFSQVQVCTAAGLSLGIILSLALAGILGICIVVVSIWLFRRKSIKKGDNKGVIYKPA

HCAVIII  TKMETEAHA*
```

FIGURE 1

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 1104 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 32..1093

( i x ) FEATURE:
        ( A ) NAME/KEY: mat_peptide
        ( B ) LOCATION: 119..1093

( i x ) FEATURE:
        ( A ) NAME/KEY: misc_feature
        ( B ) LOCATION: 1013..1024
        ( D ) OTHER INFORMATION: /note= "phosphorylation site
            recognized by protein kinase C and other kinases"

( x i ) SEQUENCE DESCRIPTION: SEQ ID NO:1:

```
GCCGCGCCC  GCCCCGCAGG  AGCCCGCGAA  G ATG  CCC  CGG  CGC  AGC  CTG  CAC        52
                                     Met  Pro  Arg  Arg  Ser  Leu  His
                                     -29                 -25

GCG  GCG  GCC  GTG  CTC  CTG  CTG  GTG  ATC  TTA  AAG  GAA  CAG  CCT  TCC  AGC   100
Ala  Ala  Ala  Val  Leu  Leu  Leu  Val  Ile  Leu  Lys  Glu  Gln  Pro  Ser  Ser
          -20                      -15                      -10

CCG  GCC  CCA  GTG  AAC  GGT  TCC  AAG  TGG  ACT  TAT  TTT  GGT  CCT  GAT  GGG   148
Pro  Ala  Pro  Val  Asn  Gly  Ser  Lys  Trp  Thr  Tyr  Phe  Gly  Pro  Asp  Gly
      -5                          1                  5                      10

GAG  AAT  AGC  TGG  TCC  AAG  AAG  TAC  CCG  TCG  TGT  GGG  GGC  CTG  CTG  CAG   196
Glu  Asn  Ser  Trp  Ser  Lys  Lys  Tyr  Pro  Ser  Cys  Gly  Gly  Leu  Leu  Gln
                    15                          20                      25

TCC  CCC  ATA  GAC  CTG  CAC  AGT  GAC  ATC  CTC  CAG  TAT  GAC  GCC  AGC  CTC   244
Ser  Pro  Ile  Asp  Leu  His  Ser  Asp  Ile  Leu  Gln  Tyr  Asp  Ala  Ser  Leu
                30                      35                      40

ACG  CCC  CTC  GAG  TTC  CAA  GGC  TAC  AAT  CTG  TCT  GCC  AAC  AAG  CAG  TTT   292
Thr  Pro  Leu  Glu  Phe  Gln  Gly  Tyr  Asn  Leu  Ser  Ala  Asn  Lys  Gln  Phe
           45                      50                      55
```

| | | | | | | | | | | | | | | | | |
|---|---|---|---|---|---|---|---|---|---|---|---|---|---|---|---|---|
| CTC | CTG | ACC | AAT | AAT | GGC | CAT | TCA | GTG | AAG | CTG | AAC | CTG | CCC | TCG | GAC | 340 |
| Leu | Leu | Thr | Asn | Asn | Gly | His | Ser | Val | Lys | Leu | Asn | Leu | Pro | Ser | Asp | |
|  | 60 |  |  |  |  | 65 |  |  |  |  | 70 |  |  |  |  | |
| ATG | CAC | ATC | CAG | GGC | CTC | CAG | TCT | CGC | TAC | AGT | GCC | ACG | CAG | CTG | CAC | 388 |
| Met | His | Ile | Gln | Gly | Leu | Gln | Ser | Arg | Tyr | Ser | Ala | Thr | Gln | Leu | His | |
| 75 |  |  |  |  | 80 |  |  |  |  | 85 |  |  |  |  | 90 | |
| CTG | CAC | TGG | GGG | AAC | CCG | AAT | GAC | CCG | CAC | GGC | TCT | GAG | CAC | ACC | GTC | 436 |
| Leu | His | Trp | Gly | Asn | Pro | Asn | Asp | Pro | His | Gly | Ser | Glu | His | Thr | Val | |
|  |  |  |  | 95 |  |  |  |  | 100 |  |  |  |  | 105 |  | |
| AGC | GGA | CAG | CAC | TTC | GCC | GCC | GAG | CTG | CAC | ATT | GTC | CAT | TAT | AAC | TCA | 484 |
| Ser | Gly | Gln | His | Phe | Ala | Ala | Glu | Leu | His | Ile | Val | His | Tyr | Asn | Ser | |
|  |  |  | 110 |  |  |  |  | 115 |  |  |  |  | 120 |  |  | |
| GAC | CTT | TAT | CCT | GAC | GCC | AGC | ACT | GCC | AGC | AAC | AAG | TCA | GAA | GGC | CTC | 532 |
| Asp | Leu | Tyr | Pro | Asp | Ala | Ser | Thr | Ala | Ser | Asn | Lys | Ser | Glu | Gly | Leu | |
|  |  | 125 |  |  |  |  | 130 |  |  |  |  | 135 |  |  |  | |
| GCT | GTC | CTG | GCT | GTT | CTC | ATT | GAG | ATG | GGC | TCC | TTC | AAT | CCG | TCC | TAT | 580 |
| Ala | Val | Leu | Ala | Val | Leu | Ile | Glu | Met | Gly | Ser | Phe | Asn | Pro | Ser | Tyr | |
|  | 140 |  |  |  |  | 145 |  |  |  |  | 150 |  |  |  |  | |
| GAC | AAG | ATC | TTC | AGT | CAC | CTT | CAA | CAT | GTA | AAG | TAC | AAA | GGC | CAG | GAA | 628 |
| Asp | Lys | Ile | Phe | Ser | His | Leu | Gln | His | Val | Lys | Tyr | Lys | Gly | Gln | Glu | |
| 155 |  |  |  |  | 160 |  |  |  |  | 165 |  |  |  |  | 170 | |
| GCA | TTC | GTC | CCG | GGA | TTC | AAC | ATT | GAA | GAG | CTG | CTT | CCG | GAG | AGG | ACC | 676 |
| Ala | Phe | Val | Pro | Gly | Phe | Asn | Ile | Glu | Glu | Leu | Leu | Pro | Glu | Arg | Thr | |
|  |  |  |  | 175 |  |  |  |  | 180 |  |  |  |  | 185 |  | |
| GCT | GAA | TAT | TAC | CGC | TAC | CGG | GGG | TCC | CTG | ACC | ACA | CCC | CCT | TGC | AAC | 724 |
| Ala | Glu | Tyr | Tyr | Arg | Tyr | Arg | Gly | Ser | Leu | Thr | Thr | Pro | Pro | Cys | Asn | |
|  |  |  | 190 |  |  |  |  | 195 |  |  |  |  | 200 |  |  | |
| CCC | ACT | GTG | CTC | TGG | ACA | GTT | TTC | CGA | AAC | CCC | GTG | CAA | ATT | TCC | CAG | 772 |
| Pro | Thr | Val | Leu | Trp | Thr | Val | Phe | Arg | Asn | Pro | Val | Gln | Ile | Ser | Gln | |
|  |  | 205 |  |  |  |  | 210 |  |  |  |  | 215 |  |  |  | |
| GAG | CAG | CTG | CTG | GCT | TTG | GAG | ACA | GCC | CTG | TAC | TGC | ACA | CAC | ATG | GAC | 820 |
| Glu | Gln | Leu | Leu | Ala | Leu | Glu | Thr | Ala | Leu | Tyr | Cys | Thr | His | Met | Asp | |
|  | 220 |  |  |  |  | 225 |  |  |  |  | 230 |  |  |  |  | |
| GAC | CCT | TCC | CCC | AGA | GAA | ATG | ATC | AAC | AAC | TTC | CGG | CAG | GTC | CAG | AAG | 868 |
| Asp | Pro | Ser | Pro | Arg | Glu | Met | Ile | Asn | Asn | Phe | Arg | Gln | Val | Gln | Lys | |
| 235 |  |  |  |  | 240 |  |  |  |  | 245 |  |  |  |  | 250 | |
| TTC | GAT | GAG | AGG | CTG | GTA | TAC | ACC | TCC | TTC | TCC | CAA | GTG | CAA | GTC | TGT | 916 |
| Phe | Asp | Glu | Arg | Leu | Val | Tyr | Thr | Ser | Phe | Ser | Gln | Val | Gln | Val | Cys | |
|  |  |  |  | 255 |  |  |  |  | 260 |  |  |  |  | 265 |  | |
| ACT | GCG | GCA | GGA | CTG | AGT | CTG | GGC | ATC | ATC | CTC | TCA | CTG | GCC | CTG | GCT | 964 |
| Thr | Ala | Ala | Gly | Leu | Ser | Leu | Gly | Ile | Ile | Leu | Ser | Leu | Ala | Leu | Ala | |
|  |  |  | 270 |  |  |  |  | 275 |  |  |  |  | 280 |  |  | |
| GGC | ATT | CTT | GGC | ATC | TGT | ATT | GTG | GTG | GTG | GTG | TCC | ATT | TGG | CTT | TTC | 1012 |
| Gly | Ile | Leu | Gly | Ile | Cys | Ile | Val | Val | Val | Val | Ser | Ile | Trp | Leu | Phe | |
|  |  | 285 |  |  |  |  | 290 |  |  |  |  | 295 |  |  |  | |
| AGA | AGG | AAG | AGT | ATC | AAA | AAA | GGT | GAT | AAC | AAG | GGA | GTC | ATT | TAC | AAG | 1060 |
| Arg | Arg | Lys | Ser | Ile | Lys | Lys | Gly | Asp | Asn | Lys | Gly | Val | Ile | Tyr | Lys | |
|  | 300 |  |  |  |  | 305 |  |  |  |  | 310 |  |  |  |  | |
| CCA | GCC | ACC | AAG | ATG | GAG | ACT | GAG | GCC | CAC | GCT | TGAGGTCCCC G | | | | | 1104 |
| Pro | Ala | Thr | Lys | Met | Glu | Thr | Glu | Ala | His | Ala | | | | | | |
| 315 |  |  |  |  | 320 |  |  |  |  | 325 | | | | | | |

( 2 ) INFORMATION FOR SEQ ID NO:2:

( i ) SEQUENCE CHARACTERISTICS:
        ( A ) LENGTH: 354 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | |
|---|---|---|---|---|---|---|---|---|---|---|---|---|---|
| Met -29 | Pro | Arg | Arg | Ser -25 | Leu | His | Ala | Ala | Ala -20 | Val | Leu | Leu | Val Ile -15 |
| Leu | Lys | Glu | Gln -10 | Pro | Ser | Ser | Pro | Ala -5 | Pro | Val | Asn | Gly | Ser Lys Trp 1 |
| Thr | Tyr 5 | Phe | Gly | Pro | Asp | Gly 10 | Glu | Asn | Ser | Trp | Ser 15 | Lys | Lys Tyr Pro |
| Ser 20 | Cys | Gly | Gly | Leu | Leu 25 | Gln | Ser | Pro | Ile | Asp 30 | Leu | His | Ser Asp Ile 35 |
| Leu | Gln | Tyr | Asp | Ala 40 | Ser | Leu | Thr | Pro | Leu 45 | Glu | Phe | Gln | Gly Tyr Asn 50 |
| Leu | Ser | Ala | Asn 55 | Lys | Gln | Phe | Leu | Leu 60 | Thr | Asn | Asn | Gly | His Ser Val 65 |
| Lys | Leu | Asn 70 | Leu | Pro | Ser | Asp | Met 75 | His | Ile | Gln | Gly | Leu 80 | Gln Ser Arg |
| Tyr | Ser 85 | Ala | Thr | Gln | Leu | His 90 | Leu | His | Trp | Gly | Asn 95 | Pro | Asn Asp Pro |
| His 100 | Gly | Ser | Glu | His | Thr 105 | Val | Ser | Gly | Gln | His 110 | Phe | Ala | Ala Glu Leu 115 |
| His | Ile | Val | His | Tyr 120 | Asn | Ser | Asp | Leu | Tyr 125 | Pro | Asp | Ala | Ser Thr Ala 130 |
| Ser | Asn | Lys | Ser 135 | Glu | Gly | Leu | Ala | Val 140 | Leu | Ala | Val | Leu | Ile Glu Met 145 |
| Gly | Ser | Phe 150 | Asn | Pro | Ser | Tyr | Asp 155 | Lys | Ile | Phe | Ser | His 160 | Leu Gln His |
| Val | Lys 165 | Tyr | Lys | Gly | Gln | Glu 170 | Ala | Phe | Val | Pro | Gly 175 | Phe | Asn Ile Glu |
| Glu 180 | Leu | Leu | Pro | Glu | Arg 185 | Thr | Ala | Glu | Tyr | Tyr 190 | Arg | Tyr | Arg Gly Ser 195 |
| Leu | Thr | Thr | Pro | Pro 200 | Cys | Asn | Pro | Thr | Val 205 | Leu | Trp | Thr | Val Phe Arg 210 |
| Asn | Pro | Val | Gln 215 | Ile | Ser | Gln | Glu | Gln 220 | Leu | Leu | Ala | Leu 225 | Glu Thr Ala |
| Leu | Tyr | Cys 230 | Thr | His | Met | Asp | Asp 235 | Pro | Ser | Pro | Arg | Glu 240 | Met Ile Asn |
| Asn | Phe 245 | Arg | Gln | Val | Gln | Lys 250 | Phe | Asp | Glu | Arg | Leu 255 | Val | Tyr Thr Ser |
| Phe 260 | Ser | Gln | Val | Gln | Val 265 | Cys | Thr | Ala | Ala | Gly 270 | Leu | Ser | Leu Gly Ile 275 |
| Ile | Leu | Ser | Leu | Ala 280 | Leu | Ala | Gly | Ile | Leu 285 | Gly | Ile | Cys | Ile Val Val 290 |
| Val | Val | Ser | Ile 295 | Trp | Leu | Phe | Arg | Arg 300 | Lys | Ser | Ile | Lys 305 | Lys Gly Asp |
| Asn | Lys | Gly 310 | Val | Ile | Tyr | Lys | Pro 315 | Ala | Thr | Lys | Met | Glu 320 | Thr Glu Ala |
| His | Ala 325 | | | | | | | | | | | | |

(2) INFORMATION FOR SEQ ID NO:3:

(i) SEQUENCE CHARACTERISTICS:
        (A) LENGTH: 986 base pairs
        (B) TYPE: nucleic acid
        (C) STRANDEDNESS: both
        (D) TOPOLOGY: linear (ii) MOLECULE TYPE: cDNA (ix) FEATURE:
    (A) NAME/KEY: CDS
    (B) LOCATION: 1..975

(ix) FEATURE:
    (A) NAME/KEY: misc_feature
    (B) LOCATION: 895..906
    (D) OTHER INFORMATION: /note= "phosphorylation site recognized by protein C kinase and other kinases"

(xi) SEQUENCE DESCRIPTION: SEQ ID NO:3:

| | | | | | | | | | | | | | | | | |
|---|---|---|---|---|---|---|---|---|---|---|---|---|---|---|---|---|
| TCC | AAG | TGG | ACT | TAT | TTT | GGT | CCT | GAT | GGG | GAG | AAT | AGC | TGG | TCC | AAG | 48 |
| Ser | Lys | Trp | Thr | Tyr | Phe | Gly | Pro | Asp | Gly | Glu | Asn | Ser | Trp | Ser | Lys | |
| 1 | | | | 5 | | | | | 10 | | | | | 15 | | |
| AAG | TAC | CCG | TCG | TGT | GGG | GGC | CTG | CTG | CAG | TCC | CCC | ATA | GAC | CTG | CAC | 96 |
| Lys | Tyr | Pro | Ser | Cys | Gly | Gly | Leu | Leu | Gln | Ser | Pro | Ile | Asp | Leu | His | |
| | | | 20 | | | | | 25 | | | | | 30 | | | |
| AGT | GAC | ATC | CTC | CAG | TAT | GAC | GCC | AGC | CTC | ACG | CCC | CTC | GAG | TTC | CAA | 144 |
| Ser | Asp | Ile | Leu | Gln | Tyr | Asp | Ala | Ser | Leu | Thr | Pro | Leu | Glu | Phe | Gln | |
| | | 35 | | | | | 40 | | | | | 45 | | | | |
| GGC | TAC | AAT | CTG | TCT | GCC | AAC | AAG | CAG | TTT | CTC | CTG | ACC | AAC | AAT | GGC | 192 |
| Gly | Tyr | Asn | Leu | Ser | Ala | Asn | Lys | Gln | Phe | Leu | Leu | Thr | Asn | Asn | Gly | |
| | 50 | | | | | 55 | | | | | 60 | | | | | |
| CAT | TCA | GTG | AAG | CTG | AAC | CTG | CCC | TCG | GAC | ATG | CAC | ATC | CAG | GGC | CTC | 240 |
| His | Ser | Val | Lys | Leu | Asn | Leu | Pro | Ser | Asp | Met | His | Ile | Gln | Gly | Leu | |
| 65 | | | | | 70 | | | | | 75 | | | | | 80 | |
| CAG | TCT | CGC | TAC | AGT | GCC | ACG | CAG | CTG | CAC | CTG | CAC | TGG | GGG | AAC | CCG | 288 |
| Gln | Ser | Arg | Tyr | Ser | Ala | Thr | Gln | Leu | His | Leu | His | Trp | Gly | Asn | Pro | |
| | | | | 85 | | | | | 90 | | | | | 95 | | |
| AAT | GAC | CCG | CAC | GGC | TCT | GAG | CAC | ACC | GTC | AGC | GGA | CAG | CAC | TTC | GCC | 336 |
| Asn | Asp | Pro | His | Gly | Ser | Glu | His | Thr | Val | Ser | Gly | Gln | His | Phe | Ala | |
| | | | 100 | | | | | 105 | | | | | 110 | | | |
| GCC | GAG | CTG | CAC | ATT | GTC | CAT | TAT | AAC | TCA | GAC | CTT | TAT | CCT | GAC | GCC | 384 |
| Ala | Glu | Leu | His | Ile | Val | His | Tyr | Asn | Ser | Asp | Leu | Tyr | Pro | Asp | Ala | |
| | | 115 | | | | | 120 | | | | | 125 | | | | |
| AGC | ACT | GCC | AGC | AAC | AAG | TCA | GAA | GGC | CTC | GCT | GTC | CTG | GCT | GTT | CTC | 432 |
| Ser | Thr | Ala | Ser | Asn | Lys | Ser | Glu | Gly | Leu | Ala | Val | Leu | Ala | Val | Leu | |
| | 130 | | | | | 135 | | | | | 140 | | | | | |
| ATT | GAG | ATG | GGC | TCC | TTC | AAT | CCG | TCC | TAT | GAC | AAG | ATC | TTC | AGT | CAC | 480 |
| Ile | Glu | Met | Gly | Ser | Phe | Asn | Pro | Ser | Tyr | Asp | Lys | Ile | Phe | Ser | His | |
| 145 | | | | | 150 | | | | | 155 | | | | | 160 | |
| CTT | CAA | CAT | GTA | AAG | TAC | AAA | GGC | CAG | GAA | GCA | TTC | GTC | CCG | GGA | TTC | 528 |
| Leu | Gln | His | Val | Lys | Tyr | Lys | Gly | Gln | Glu | Ala | Phe | Val | Pro | Gly | Phe | |
| | | | | 165 | | | | | 170 | | | | | 175 | | |
| AAC | ATT | GAA | GAG | CTG | CTT | CCG | GAG | AGG | ACC | GCT | GAA | TAT | TAC | CGC | TAC | 576 |
| Asn | Ile | Glu | Glu | Leu | Leu | Pro | Glu | Arg | Thr | Ala | Glu | Tyr | Tyr | Arg | Tyr | |
| | | | 180 | | | | | 185 | | | | | 190 | | | |
| CGG | GGG | TCC | CTG | ACC | ACA | CCC | CCT | TGC | AAC | CCC | ACT | GTG | CTC | TGG | ACA | 624 |
| Arg | Gly | Ser | Leu | Thr | Thr | Pro | Pro | Cys | Asn | Pro | Thr | Val | Leu | Trp | Thr | |
| | | 195 | | | | | 200 | | | | | 205 | | | | |
| GTT | TTC | CGA | AAC | CCC | GTG | CAA | ATT | TCC | CAG | GAG | CAG | CTG | CTG | GCT | TTG | 672 |
| Val | Phe | Arg | Asn | Pro | Val | Gln | Ile | Ser | Gln | Glu | Gln | Leu | Leu | Ala | Leu | |
| | 210 | | | | | 215 | | | | | 220 | | | | | |
| GAG | ACA | GCC | CTG | TAC | TGC | ACA | CAC | ATG | GAC | GAC | CCT | TCC | CCC | AGA | GAA | 720 |
| Glu | Thr | Ala | Leu | Tyr | Cys | Thr | His | Met | Asp | Asp | Pro | Ser | Pro | Arg | Glu | |
| 225 | | | | | 230 | | | | | 235 | | | | | 240 | |
| ATG | ATC | AAC | AAC | TTC | CGG | CAG | GTC | CAG | AAG | TTC | GAT | GAG | AGG | CTG | GTA | 768 |
| Met | Ile | Asn | Asn | Phe | Arg | Gln | Val | Gln | Lys | Phe | Asp | Glu | Arg | Leu | Val | |
| | | | | 245 | | | | | 250 | | | | | 255 | | |
| TAC | ACC | TCC | TTC | TCC | CAA | GTG | CAA | GTC | TGT | ACT | GCG | GCA | GGA | CTG | AGT | 816 |
| Tyr | Thr | Ser | Phe | Ser | Gln | Val | Gln | Val | Cys | Thr | Ala | Ala | Gly | Leu | Ser | |
| | | | 260 | | | | | 265 | | | | | 270 | | | |

```
CTG GGC ATC ATC CTC TCA CTG GCC CTG GCT GGC ATT CTT GGC ATC TGT      864
Leu Gly Ile Ile Leu Ser Leu Ala Leu Ala Gly Ile Leu Gly Ile Cys
        275                 280                 285

ATT GTG GTG GTG GTG TCC ATT TGG CTT TTC AGA AGG AAG AGT ATC AAA      912
Ile Val Val Val Val Ser Ile Trp Leu Phe Arg Arg Lys Ser Ile Lys
        290                 295                 300

AAA GGT GAT AAC AAG GGA GTC ATT TAC AAG CCA GCC ACC AAG ATG GAG      960
Lys Gly Asp Asn Lys Gly Val Ile Tyr Lys Pro Ala Thr Lys Met Glu
305                 310                 315                 320

ACT GAG GCC CAC GCT TGAGGTCCCC G                                      986
Thr Glu Ala His Ala
                325
```

( 2 ) INFORMATION FOR SEQ ID NO:4:

( i ) SEQUENCE CHARACTERISTICS:
        ( A ) LENGTH: 325 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Ser Lys Trp Thr Tyr Phe Gly Pro Asp Gly Glu Asn Ser Trp Ser Lys
1                   5                   10                  15

Lys Tyr Pro Ser Cys Gly Gly Leu Leu Gln Ser Pro Ile Asp Leu His
                20                  25                  30

Ser Asp Ile Leu Gln Tyr Asp Ala Ser Leu Thr Pro Leu Glu Phe Gln
            35                  40                  45

Gly Tyr Asn Leu Ser Ala Asn Lys Gln Phe Leu Leu Thr Asn Asn Gly
        50                  55                  60

His Ser Val Lys Leu Asn Leu Pro Ser Asp Met His Ile Gln Gly Leu
65                  70                  75                  80

Gln Ser Arg Tyr Ser Ala Thr Gln Leu His Leu His Trp Gly Asn Pro
                85                  90                  95

Asn Asp Pro His Gly Ser Glu His Thr Val Ser Gly Gln His Phe Ala
                100                 105                 110

Ala Glu Leu His Ile Val His Tyr Asn Ser Asp Leu Tyr Pro Asp Ala
            115                 120                 125

Ser Thr Ala Ser Asn Lys Ser Glu Gly Leu Ala Val Leu Ala Val Leu
        130                 135                 140

Ile Glu Met Gly Ser Phe Asn Pro Ser Tyr Asp Lys Ile Phe Ser His
145                 150                 155                 160

Leu Gln His Val Lys Tyr Lys Gly Gln Glu Ala Phe Val Pro Gly Phe
                165                 170                 175

Asn Ile Glu Glu Leu Leu Pro Glu Arg Thr Ala Glu Tyr Tyr Arg Tyr
                180                 185                 190

Arg Gly Ser Leu Thr Thr Pro Pro Cys Asn Pro Thr Val Leu Trp Thr
            195                 200                 205

Val Phe Arg Asn Pro Val Gln Ile Ser Gln Glu Gln Leu Leu Ala Leu
        210                 215                 220

Glu Thr Ala Leu Tyr Cys Thr His Met Asp Asp Pro Ser Pro Arg Glu
225                 230                 235                 240

Met Ile Asn Asn Phe Arg Gln Val Gln Lys Phe Asp Glu Arg Leu Val
                245                 250                 255

Tyr Thr Ser Phe Ser Gln Val Gln Val Cys Thr Ala Ala Gly Leu Ser
                260                 265                 270

Leu Gly Ile Ile Leu Ser Leu Ala Leu Ala Gly Ile Leu Gly Ile Cys
```

|  | 275 |  |  |  |  | 280 |  |  |  |  | 285 |  |  |
|---|---|---|---|---|---|---|---|---|---|---|---|---|---|
| Ile | Val | Val | Val | Val | Ser | Ile | Trp | Leu | Phe | Arg | Arg | Lys | Ser | Ile | Lys |
|  | 290 |  |  |  |  | 295 |  |  |  |  | 300 |  |  |
| Lys | Gly | Asp | Asn | Lys | Gly | Val | Ile | Tyr | Lys | Pro | Ala | Thr | Lys | Met | Glu |
| 305 |  |  |  |  | 310 |  |  |  |  | 315 |  |  |  |  | 320 |
| Thr | Glu | Ala | His | Ala |
|  |  |  |  | 325 |

(2) INFORMATION FOR SEQ ID NO:5:

( i ) SEQUENCE CHARACTERISTICS:
        ( A ) LENGTH: 12 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 1..12

( x i ) SEQUENCE DESCRIPTION: SEQ ID NO:5:

AGA AGG AAG AGT                                          12
Arg Arg Lys Ser
 1

(2) INFORMATION FOR SEQ ID NO:6:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

Arg Arg Lys Ser
 1

(2) INFORMATION FOR SEQ ID NO:7:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

TGAGTCGACG                                                10

(2) INFORMATION FOR SEQ ID NO:8:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

AATTCGTCGA CTCA                                      14

(2) INFORMATION FOR SEQ ID NO:9:

( i ) SEQUENCE CHARACTERISTICS:
    ( A ) LENGTH: 813 base pairs
    ( B ) TYPE: nucleic acid
    ( C ) STRANDEDNESS: both
    ( D ) TOPOLOGY: linear ( i i ) MOLECULE TYPE: cDNA ( i x ) FEATURE:
    ( A ) NAME/KEY: CDS
    ( B ) LOCATION: 1..813

( x i ) SEQUENCE DESCRIPTION: SEQ ID NO:9:

```
TCC  AAG  TGG  ACT  TAT  TTT  GGT  CCT  GAT  GGG  GAG  AAT  AGC  TGG  TCC  AAG         48
Ser  Lys  Trp  Thr  Tyr  Phe  Gly  Pro  Asp  Gly  Glu  Asn  Ser  Trp  Ser  Lys
 1               5                        10                       15

AAG  TAC  CCG  TCG  TGT  GGG  GGC  CTG  CTG  CAG  TCC  CCC  ATA  GAC  CTG  CAC         96
Lys  Tyr  Pro  Ser  Cys  Gly  Gly  Leu  Leu  Gln  Ser  Pro  Ile  Asp  Leu  His
              20                       25                       30

AGT  GAC  ATC  CTC  CAG  TAT  GAC  GCC  AGC  CTC  ACG  CCC  CTC  GAG  TTC  CAA        144
Ser  Asp  Ile  Leu  Gln  Tyr  Asp  Ala  Ser  Leu  Thr  Pro  Leu  Glu  Phe  Gln
         35                       40                       45

GGC  TAC  AAT  CTG  TCT  GCC  AAC  AAG  CAG  TTT  CTC  CTG  ACC  AAC  AAT  GGC        192
Gly  Tyr  Asn  Leu  Ser  Ala  Asn  Lys  Gln  Phe  Leu  Leu  Thr  Asn  Asn  Gly
     50                       55                       60

CAT  TCA  GTG  AAG  CTG  AAC  CTG  CCC  TCG  GAC  ATG  CAC  ATC  CAG  GGC  CTC        240
His  Ser  Val  Lys  Leu  Asn  Leu  Pro  Ser  Asp  Met  His  Ile  Gln  Gly  Leu
 65                       70                       75                       80

CAG  TCT  CGC  TAC  AGT  GCC  ACG  CAG  CTG  CAC  CTG  CAC  TGG  GGG  AAC  CCG        288
Gln  Ser  Arg  Tyr  Ser  Ala  Thr  Gln  Leu  His  Leu  His  Trp  Gly  Asn  Pro
              85                       90                       95

AAT  GAC  CCG  CAC  GGC  TCT  GAG  CAC  ACC  GTC  AGC  GGA  CAG  CAC  TTC  GCC        336
Asn  Asp  Pro  His  Gly  Ser  Glu  His  Thr  Val  Ser  Gly  Gln  His  Phe  Ala
         100                      105                      110

GCC  GAG  CTG  CAC  ATT  GTC  CAT  TAT  AAC  TCA  GAC  CTT  TAT  CCT  GAC  GCC        384
Ala  Glu  Leu  His  Ile  Val  His  Tyr  Asn  Ser  Asp  Leu  Tyr  Pro  Asp  Ala
              115                      120                      125

AGC  ACT  GCC  AGC  AAC  AAG  TCA  GAA  GGC  CTC  GCT  GTC  CTG  GCT  GTT  CTC        432
Ser  Thr  Ala  Ser  Asn  Lys  Ser  Glu  Gly  Leu  Ala  Val  Leu  Ala  Val  Leu
     130                      135                      140

ATT  GAG  ATG  GGC  TCC  TTC  AAT  CCG  TCC  TAT  GAC  AAG  ATC  TTC  AGT  CAC        480
Ile  Glu  Met  Gly  Ser  Phe  Asn  Pro  Ser  Tyr  Asp  Lys  Ile  Phe  Ser  His
145                      150                      155                      160

CTT  CAA  CAT  GTA  AAG  TAC  AAA  GGC  CAG  GAA  GCA  TTC  GTC  CCG  GGA  TTC        528
Leu  Gln  His  Val  Lys  Tyr  Lys  Gly  Gln  Glu  Ala  Phe  Val  Pro  Gly  Phe
              165                      170                      175

AAC  ATT  GAA  GAG  CTG  CTT  CCG  GAG  AGG  ACC  GCT  GAA  TAT  TAC  CGC  TAC        576
Asn  Ile  Glu  Glu  Leu  Leu  Pro  Glu  Arg  Thr  Ala  Glu  Tyr  Tyr  Arg  Tyr
         180                      185                      190

CGG  GGG  TCC  CTG  ACC  ACA  CCC  CCT  TGC  AAC  CCC  ACT  GTG  CTC  TGG  ACA        624
Arg  Gly  Ser  Leu  Thr  Thr  Pro  Pro  Cys  Asn  Pro  Thr  Val  Leu  Trp  Thr
              195                      200                      205

GTT  TTC  CGA  AAC  CCC  GTG  CAA  ATT  TCC  CAG  GAG  CAG  CTG  CTG  GCT  TTG        672
Val  Phe  Arg  Asn  Pro  Val  Gln  Ile  Ser  Gln  Glu  Gln  Leu  Leu  Ala  Leu
     210                      215                      220

GAG  ACA  GCC  CTG  TAC  TGC  ACA  CAC  ATG  GAC  GAC  CCT  TCC  CCC  AGA  GAA        720
Glu  Thr  Ala  Leu  Tyr  Cys  Thr  His  Met  Asp  Asp  Pro  Ser  Pro  Arg  Glu
225                      230                      235                      240

ATG  ATC  AAC  AAC  TTC  CGG  CAG  GTC  CAG  AAG  TTC  GAT  GAG  AGG  CTG  GTA        768
Met  Ile  Asn  Asn  Phe  Arg  Gln  Val  Gln  Lys  Phe  Asp  Glu  Arg  Leu  Val
              245                      250                      255

TAC  ACC  TCC  TTC  TCC  CAA  GTG  CAA  GTC  TGT  ACT  GCG  GCA  GGA  CTG              813
Tyr  Thr  Ser  Phe  Ser  Gln  Val  Gln  Val  Cys  Thr  Ala  Ala  Gly  Leu
```

( 2 ) INFORMATION FOR SEQ ID NO:10:

( i ) SEQUENCE CHARACTERISTICS:
        ( A ) LENGTH: 271 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Ser Lys Trp Thr Tyr Phe Gly Pro Asp Gly Glu Asn Ser Trp Ser Lys
 1               5                  10                  15
Lys Tyr Pro Ser Cys Gly Gly Leu Leu Gln Ser Pro Ile Asp Leu His
            20                  25                  30
Ser Asp Ile Leu Gln Tyr Asp Ala Ser Leu Thr Pro Leu Glu Phe Gln
            35                  40                  45
Gly Tyr Asn Leu Ser Ala Asn Lys Gln Phe Leu Leu Thr Asn Asn Gly
        50                  55                  60
His Ser Val Lys Leu Asn Leu Pro Ser Asp Met His Ile Gln Gly Leu
 65                 70                  75                  80
Gln Ser Arg Tyr Ser Ala Thr Gln Leu His Leu His Trp Gly Asn Pro
                85                  90                  95
Asn Asp Pro His Gly Ser Glu His Thr Val Ser Gly Gln His Phe Ala
            100                 105                 110
Ala Glu Leu His Ile Val His Tyr Asn Ser Asp Leu Tyr Pro Asp Ala
            115                 120                 125
Ser Thr Ala Ser Asn Lys Ser Glu Gly Leu Ala Val Leu Ala Val Leu
        130                 135                 140
Ile Glu Met Gly Ser Phe Asn Pro Ser Tyr Asp Lys Ile Phe Ser His
145                 150                 155                 160
Leu Gln His Val Lys Tyr Lys Gly Gln Glu Ala Phe Val Pro Gly Phe
                165                 170                 175
Asn Ile Glu Glu Leu Leu Pro Glu Arg Thr Ala Glu Tyr Tyr Arg Tyr
            180                 185                 190
Arg Gly Ser Leu Thr Thr Pro Pro Cys Asn Pro Thr Val Leu Trp Thr
        195                 200                 205
Val Phe Arg Asn Pro Val Gln Ile Ser Gln Glu Gln Leu Leu Ala Leu
    210                 215                 220
Glu Thr Ala Leu Tyr Cys Thr His Met Asp Asp Pro Ser Pro Arg Glu
225                 230                 235                 240
Met Ile Asn Asn Phe Arg Gln Val Gln Lys Phe Asp Glu Arg Leu Val
                245                 250                 255
Tyr Thr Ser Phe Ser Gln Val Gln Val Cys Thr Ala Ala Gly Leu
            260                 265                 270
```

( 2 ) INFORMATION FOR SEQ ID NO:11:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

CTTTTTTGAT ACCCTTCCTT CTGAA                       25

( 2 ) INFORMATION FOR SEQ ID NO:12:

( i ) SEQUENCE CHARACTERISTICS:
        ( A ) LENGTH: 986 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 1..975

( x i ) SEQUENCE DESCRIPTION: SEQ ID NO:12:

```
TCC  AAG  TGG  ACT  TAT  TTT  GGT  CCT  GAT  GGG  GAG  AAT  AGC  TGG  TCC  AAG        48
Ser  Lys  Trp  Thr  Tyr  Phe  Gly  Pro  Asp  Gly  Glu  Asn  Ser  Trp  Ser  Lys
 1              5                        10                       15

AAG  TAC  CCG  TCG  TGT  GGG  GGC  CTG  CTG  CAG  TCC  CCC  ATA  GAC  CTG  CAC        96
Lys  Tyr  Pro  Ser  Cys  Gly  Gly  Leu  Leu  Gln  Ser  Pro  Ile  Asp  Leu  His
              20                        25                  30

AGT  GAC  ATC  CTC  CAG  TAT  GAC  GCC  AGC  CTC  ACG  CCC  CTC  GAG  TTC  CAA       144
Ser  Asp  Ile  Leu  Gln  Tyr  Asp  Ala  Ser  Leu  Thr  Pro  Leu  Glu  Phe  Gln
              35                        40                  45

GGC  TAC  AAT  CTG  TCT  GCC  AAC  AAG  CAG  TTT  CTC  CTG  ACC  AAC  AAT  GGC       192
Gly  Tyr  Asn  Leu  Ser  Ala  Asn  Lys  Gln  Phe  Leu  Leu  Thr  Asn  Asn  Gly
 50                        55                       60

CAT  TCA  GTG  AAG  CTG  AAC  CTG  CCC  TCG  GAC  ATG  CAC  ATC  CAG  GGC  CTC       240
His  Ser  Val  Lys  Leu  Asn  Leu  Pro  Ser  Asp  Met  His  Ile  Gln  Gly  Leu
 65                        70                       75                       80

CAG  TCT  CGC  TAC  AGT  GCC  ACG  CAG  CTG  CAC  CTG  CAC  TGG  GGG  AAC  CCG       288
Gln  Ser  Arg  Tyr  Ser  Ala  Thr  Gln  Leu  His  Leu  His  Trp  Gly  Asn  Pro
              85                        90                  95

AAT  GAC  CCG  CAC  GGC  TCT  GAG  CAC  ACC  GTC  AGC  GGA  CAG  CAC  TTC  GCC       336
Asn  Asp  Pro  His  Gly  Ser  Glu  His  Thr  Val  Ser  Gly  Gln  His  Phe  Ala
              100                       105                 110

GCC  GAG  CTG  CAC  ATT  GTC  CAT  TAT  AAC  TCA  GAC  CTT  TAT  CCT  GAC  GCC       384
Ala  Glu  Leu  His  Ile  Val  His  Tyr  Asn  Ser  Asp  Leu  Tyr  Pro  Asp  Ala
              115                       120                 125

AGC  ACT  GCC  AGC  AAC  AAG  TCA  GAA  GGC  CTC  GCT  GTC  CTG  GCT  GTT  CTC       432
Ser  Thr  Ala  Ser  Asn  Lys  Ser  Glu  Gly  Leu  Ala  Val  Leu  Ala  Val  Leu
              130                       135                 140

ATT  GAG  ATG  GGC  TCC  TTC  AAT  CCG  TCC  TAT  GAC  AAG  ATC  TTC  AGT  CAC       480
Ile  Glu  Met  Gly  Ser  Phe  Asn  Pro  Ser  Tyr  Asp  Lys  Ile  Phe  Ser  His
145                       150                       155                      160

CTT  CAA  CAT  GTA  AAG  TAC  AAA  GGC  CAG  GAA  GCA  TTC  GTC  CCG  GGA  TTC       528
Leu  Gln  His  Val  Lys  Tyr  Lys  Gly  Gln  Glu  Ala  Phe  Val  Pro  Gly  Phe
              165                       170                 175

AAC  ATT  GAA  GAG  CTG  CTT  CCG  GAG  AGG  ACC  GCT  GAA  TAT  TAC  CGC  TAC       576
Asn  Ile  Glu  Glu  Leu  Leu  Pro  Glu  Arg  Thr  Ala  Glu  Tyr  Tyr  Arg  Tyr
              180                       185                 190

CGG  GGG  TCC  CTG  ACC  ACA  CCC  CCT  TGC  AAC  CCC  ACT  GTG  CTC  TGG  ACA       624
Arg  Gly  Ser  Leu  Thr  Thr  Pro  Pro  Cys  Asn  Pro  Thr  Val  Leu  Trp  Thr
              195                       200                 205

GTT  TTC  CGA  AAC  CCC  GTG  CAA  ATT  TCC  CAG  GAG  CAG  CTG  CTG  GCT  TTG       672
Val  Phe  Arg  Asn  Pro  Val  Gln  Ile  Ser  Gln  Glu  Gln  Leu  Leu  Ala  Leu
210                       215                       220

GAG  ACA  GCC  CTG  TAC  TGC  ACA  CAC  ATG  GAC  GAC  CCT  TCC  CCC  AGA  GAA       720
Glu  Thr  Ala  Leu  Tyr  Cys  Thr  His  Met  Asp  Asp  Pro  Ser  Pro  Arg  Glu
225                       230                       235                      240

ATG  ATC  AAC  AAC  TTC  CGG  CAG  GTC  CAG  AAG  TTC  GAT  GAG  AGG  CTG  GTA       768
Met  Ile  Asn  Asn  Phe  Arg  Gln  Val  Gln  Lys  Phe  Asp  Glu  Arg  Leu  Val
              245                       250                 255
```

```
TAC  ACC  TCC  TTC  TCC  CAA  GTG  CAA  GTC  TGT  ACT  GCG  GCA  GGA  CTG  AGT        816
Tyr  Thr  Ser  Phe  Ser  Gln  Val  Gln  Val  Cys  Thr  Ala  Ala  Gly  Leu  Ser
               260                 265                           270

CTG  GGC  ATC  ATC  CTC  TCA  CTG  GCC  CTG  GCT  GGC  ATT  CTT  GGC  ATC  TGT        864
Leu  Gly  Ile  Ile  Leu  Ser  Leu  Ala  Leu  Ala  Gly  Ile  Leu  Gly  Ile  Cys
          275                      280                           285

ATT  GTG  GTG  GTG  GTG  TCC  ATT  TGG  CTT  TTC  AGA  AGG  AAG  GGT  ATC  AAA        912
Ile  Val  Val  Val  Val  Ser  Ile  Trp  Leu  Phe  Arg  Arg  Lys  Gly  Ile  Lys
     290                           295                     300

AAA  GGT  GAT  AAC  AAG  GGA  GTC  ATT  TAC  AAG  CCA  GCC  ACC  AAG  ATG  GAG        960
Lys  Gly  Asp  Asn  Lys  Gly  Val  Ile  Tyr  Lys  Pro  Ala  Thr  Lys  Met  Glu
305                      310                      315                      320

ACT  GAG  GCC  CAC  GCT  TGAGGTCCCC G                                                 986
Thr  Glu  Ala  His  Ala
                    325
```

( 2 ) INFORMATION FOR SEQ ID NO:13:

( i ) SEQUENCE CHARACTERISTICS:
        ( A ) LENGTH: 325 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
Ser  Lys  Trp  Thr  Tyr  Phe  Gly  Pro  Asp  Gly  Glu  Asn  Ser  Trp  Ser  Lys
  1             5                      10                          15

Lys  Tyr  Pro  Ser  Cys  Gly  Gly  Leu  Leu  Gln  Ser  Pro  Ile  Asp  Leu  His
               20                      25                     30

Ser  Asp  Ile  Leu  Gln  Tyr  Asp  Ala  Ser  Leu  Thr  Pro  Leu  Glu  Phe  Gln
          35                      40                     45

Gly  Tyr  Asn  Leu  Ser  Ala  Asn  Lys  Gln  Phe  Leu  Leu  Thr  Asn  Asn  Gly
     50                      55                      60

His  Ser  Val  Lys  Leu  Asn  Leu  Pro  Ser  Asp  Met  His  Ile  Gln  Gly  Leu
 65                       70                     75                          80

Gln  Ser  Arg  Tyr  Ser  Ala  Thr  Gln  Leu  His  Leu  His  Trp  Gly  Asn  Pro
               85                           90                          95

Asn  Asp  Pro  His  Gly  Ser  Glu  His  Thr  Val  Ser  Gly  Gln  His  Phe  Ala
               100                      105                      110

Ala  Glu  Leu  His  Ile  Val  His  Tyr  Asn  Ser  Asp  Leu  Tyr  Pro  Asp  Ala
               115                      120                      125

Ser  Thr  Ala  Ser  Asn  Lys  Ser  Glu  Gly  Leu  Ala  Val  Leu  Ala  Val  Leu
     130                      135                      140

Ile  Glu  Met  Gly  Ser  Phe  Asn  Pro  Ser  Tyr  Asp  Lys  Ile  Phe  Ser  His
145                           150                      155                 160

Leu  Gln  His  Val  Lys  Tyr  Lys  Gly  Gln  Glu  Ala  Phe  Val  Pro  Gly  Phe
                    165                      170                      175

Asn  Ile  Glu  Glu  Leu  Leu  Pro  Glu  Arg  Thr  Ala  Glu  Tyr  Tyr  Arg  Tyr
               180                      185                      190

Arg  Gly  Ser  Leu  Thr  Thr  Pro  Pro  Cys  Asn  Pro  Thr  Val  Leu  Trp  Thr
          195                      200                      205

Val  Phe  Arg  Asn  Pro  Val  Gln  Ile  Ser  Gln  Glu  Gln  Leu  Leu  Ala  Leu
     210                      215                      220

Glu  Thr  Ala  Leu  Tyr  Cys  Thr  His  Met  Asp  Asp  Pro  Ser  Pro  Arg  Glu
225                      230                      235                      240

Met  Ile  Asn  Asn  Phe  Arg  Gln  Val  Gln  Lys  Phe  Asp  Glu  Arg  Leu  Val
                    245                      250                      255
```

```
Tyr Thr Ser Phe Ser Gln Val Gln Val Cys Thr Ala Ala Gly Leu Ser
            260             265                     270

Leu Gly Ile Ile Leu Ser Leu Ala Leu Ala Gly Ile Leu Gly Ile Cys
        275             280              285

Ile Val Val Val Ser Ile Trp Leu Phe Arg Arg Lys Gly Ile Lys
    290         295             300

Lys Gly Asp Asn Lys Gly Val Ile Tyr Lys Pro Ala Thr Lys Met Glu
305             310              315                     320

Thr Glu Ala His Ala
                325
```

( 2 ) INFORMATION FOR SEQ ID NO:14:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

ACATTGAAGA GCTGCTTCCG G      21

( 2 ) INFORMATION FOR SEQ ID NO:15:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

AATTTGCACG GGGTTTCGG      19

( 2 ) INFORMATION FOR SEQ ID NO:16:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

GTCCACTTGG ATCCGTTCAC TGG      23

GENE SEQUENCE AND PROBE FOR A MARKER OF NON-SMALL CELL LUNG CARINOMA

TECHNICAL FIELD

The invention relates to genes and proteins specific for certain cancers and methods for their detection.

BACKGROUND OF THE INVENTION

Lung cancer is the most common form of cancer in the world. Estimates for the year 1985 indicate that there were about 900,000 cases of lung cancer worldwide. (Parkin, et el., "Estimates of the worldwide incidence of eighteen major cancers in 1985," Int J Cancer 1993; 54:594–606). For the United States alone, 1993 projections placed the number of new lung cancer cases at 170,000, with a mortality of about 88%. (Boring, et al., "Cancer statistics," CA Cancer J Clin 1993; 43:7–26). Although the occurrence of breast cancer is slightly more common in the United States, lung cancer is second behind prostate cancer for males and third behind breast and colorectal cancers for women. Yet, lung cancer is the most common cause of cancer deaths.

The World Health Organization classifies lung cancer into four major histological types: (1) squamous cell carcinoma (SCC), (2) adenocarcinoma, (3) large cell carcinoma, and (4) small cell lung carcinoma (SCLC). (The World Health Organization, "The World Health Organization histological typing of lung tumours," Am J Clin Pathol 1982; 77:123–136). However, there is a great deal of tumor heterogeneity even within the various subtypes, and it is not uncommon for lung cancer to have features of more than one morphologic subtype. The term non-small cell lung carcinoma (NSCLC) includes squamous, adenocarcinoma and large cell carcinomas.

Typically, a combination of X-ray and sputum cytology is used to diagnose lung cancer. Unfortunately, by the time a patient seeks medical help for their symptoms, the cancer is at such an advanced state it is usually incurable. Cancer Facts and Figures (based on rates from NCI SEER Program 1977–1981), New York: American Cancer Society, 1986). Routine large-scale radiologic or cytologic screening of smokers has been investigated. Studies concluded that cytomorphological screening did not significantly reduce the mortality rate from lung cancer and was not recommended for routine use. ("Early lung cancer detection: summary & conclusions," Am Rev Respir Dis 1984; 130:565–70). However, in a subpopulation of patients where the cancer is diagnosed at a very early stage and the lung is surgically resectioned, there is a 5-year survival rate of 70–90%. (Flehinger, et al., "The effect of surgical treatment on survival from early lung cancer," Chest; 1992, 101:1013–1018; Melamed, et al,. "Screening for early lung cancer: results of the Memorial Sloan-Kettering Study in New York," Chest; 1984 86:44–53). Therefore, research has focused on early detection of tumor markers before the cancer becomes clinically apparent and while the cancer is still localized and amenable to therapy.

The identification of antigens associated with lung cancer has stimulated considerable interest because of their use in screening, diagnosis, clinical management, and potential treatment of lung cancer. International workshops have attempted to classify the lung cancer antigens into 15 possible clusters that may define histologic origins. (Souhami et al., "Antigens of lung cancer: results of the second international workshop on lung cancer antigens," JNCI 1991; 83:609–612). As of 1988, more than 200 monoclonal antibodies (MAb) have been reported to react with human lung tumors. (Radosevich, et al., "Monoclonal antibody assays for lung cancer," In: Cancer Diagnosis in Vitro Using Monoclonal Antibodies. Edited by H. A. Kupchik. New York: Marcel Dekker, 1988;101–121).

MAbs for lung cancer were first developed to distinguish NSCLC from SCLC. (Mulshine, et al., "Monoclonal antibodies that distinguish nonsmall-cell from small-cell lung cancer," J Immunol 1983; 121:497–502). In most cases, the identity of the cell surface antigen with which a particular antibody reacts is not known, or has not been well characterized. (Scott, et al., "Early lung cancer detection using monoclonal antibodies," In: Lung Cancer. Edited by J. A. Roth, J. D. Cox, and W. K. Hong. Boston: Blackwell Scientific Publications, 1993:310–324).

MAbs have been used in the immunocytochemical staining of sputum samples to predict the progression of lung cancer. (Tockman, et al., "Sensitive and specific monoclonal antibody recognition of human lung cancer antigen on preserved sputum cells: a new approach to early lung cancer detection," J Clin Oncol 1988; 6:1685–1693). In the study, two MAbs were utilized, 624H12 which binds a glycolipid antigen expressed in SCLC and 703D4 which is directed to a protein antigen of NSCLC. Of the sputum specimens from participants who progressed to lung cancer, two-thirds showed positive reactivity with either the SCLC or the NSCLC MAb. In contrast, of those that did not progress to lung cancer, 35 of 40 did not react with the SCLC or NSCLC Mab. This study suggests the need for the development of additional early detection targets to discover the onset of malignancy at the earliest possible stage.

Carcinoembryonic antigen (CEA) is a frequently studied tumor marker of cancer including lung cancer. (Nutini, et al., "Serum NSE, CEA, CT, CA 15-3 levels in human lung cancer," Int J Biol Markers 1990; 5:198–202) . Squamous cell carcinoma antigen is another established serum marker. (Margolis, et al., "Serum tumor markers in non-small cell lung cancer," Cancer 1994; 73:605–609_). Other serum antigens for lung cancer include antigens recognized by MAbs 5E8, 5C7, and 1F10, the combination of which distinguishes between patients with lung cancer from those without (Schepart, et al., "Monoclonal antibody-mediated detection of lung cancer antigens in serum," Am Rev Respir Dis 1988; 138:1434–8), Furthermore, the combination of 5E8, 5C7 and 1F10 was more sensitive, specific and accurate for identifying NSCLC when compared to results from a combination of the CEA and squamous cell carcinoma antigen tests. (Margolis, et al., Cancer 1994; 73:605–609).

Serum CA 125, initially described as an ovarian cancer-associated antigen, has been investigated for its use as a prognostic factor in NSCLC. (Diez, et al., "Prognostic significance of serum CA 125 antigen assay in patients with non-small cell lung cancer," Cancer 1994; 73:1369-76). The study determined that the preoperative serum level of CA 125 antigen is inversely correlated with survival and tumor relapse in NSCLC.

Despite the numerous examples of MAb applications, none has yet emerged that has changed clinical practice. (Mulshine, et al., "Applications of monoclonal antibodies in the treatment of solid tumors," In: Biologic Therapy of Cancer. Edited by V. T. Devita, S. Hellman, and S. A. Rosenberg. Philadelphia: JB Lippincott, 1991, pp. 563–588). MAbs alone may not be the answer to early detection because there has only been moderate success with immunologic reagents for paraffin-embedded tissue. Secondly, lung cancer may express features that cannot be differentiated by antibodies; for example, chromosomal deletions, gene amplification, or translocation and alteration in enzymatic activity.

After the gene to the MAb recognized surface antigen has been cloned, cytogenetic and molecular techniques may provide powerful tools for screening, diagnosis, management and ultimately treatment of lung cancer. An example of a lung cancer antigen that has been cloned is the adenocarcinoma-associated antigen. This antigen, recognized by KS1/4 MAb, is an epithelial malignancy/epithelial tissue glycoprotein from the human lung adenocarcinoma cell line UCLA-P3. (Strnad, et al., "Molecular cloning and characterization of a human adenocarcinoma/epithelial cell surface antigen complementary DNA," Cancer Res 1989; 49:314–317). The antigen has been found on all adenocarcinoma cells tested and in various corresponding normal epithelial cells. Northern blot analysis indicated that transcription of the adenocarcinoma-associated antigen was detected in RNA isolated from normal colon but not in RNA isolated from normal lung, prostate, or liver. Therefore identification of adenocarcinoma-associated antigen in lung cells may prove to be diagnostic for adenocarcinoma.

The cloning of CEA and the nonspecific crossreacting antigen (NCA) has allowed the development of specific DNA probes which discriminate their expression in lung cancer at the mRNA level. (Hasegawa, et al., "Nonspecific crossreacting antigen (NCA) is a major member of the CEA-related gene family expressed in lung cancer," Br J Cancer 1993; 67:58–65). NCA is a component of the CEA gene family in lung cancer and is also recognized by anti-CEA antibodies, especially polyclonal antibodies. Because of the crossreactivity, investigations to analyze CEA and NCA separately in lung disease had been difficult. The use of DNA probes determined that lung cancer cells fall into three different types according to their CEA and/or NCA expression by Northern blot analysis. Specifically, lung cancers expressed both CEA and NCAmRNA, only NCAmRNA, or neither mRNA. CEA-relatedmRNA expression was always accompanied by NCAmRNA expression and there were no cases of CEAmRNA expression alone. The separate assessment of CEA and NCA expression in lung cancers may be important in determining the prognosis of lung cancers because the antigens have been described as cell-cell adhesion molecules and may play a role in cancer metastasis.

Another method to detect the presence of an antigen gene or its mRNA in specific cells or to localize an antigen gene to a specific locus on a chromosome is in situ hybridization. In situ hybridization uses nucleic acid probes that recognize either repetitive sequences on a chromosome or sequences along the whole chromosome length or chromosome segments. By tagging the probes with radioisotopes or color detection systems, chromosome regions can be identified within the cell. Investigations using in situ hybridization have demonstrated numerous chromosomal abnormalities in samples from human tumors, including bladder, neuroectodermal, breast, gastric and lung cancer tumors. (Kim, et al., "Interphase cytogenetics in paraffin sections of lung tumors by non-isotopic in situ hybridization. Mapping Genotype/ phenotype heterogeneity," Am J Pathol 1993; 142:307–317).

Fluorescent in situ hybridization (FISH) allows cells to be stained so that genetic aberrations resulting in changes in gene copy number or structure can be quantitated by fluorescent microscopy. In this technique, a chemically labeled single-stranded nucleic acid probe homologous to the target nucleic acid sequence is annealed to denatured nucleic acid contained in target cells. The cells may be mounted on a microscope slide, in suspension or prepared from paraffin-embedded material. Treating the chemically modified probes with a fluorescent ligand makes the bound probe visible. FISH has been used for (1) detection of changes in gene copy number and gene structure; (2) detection of genetic changes, even in low frequency subpopulations; and (3) detection and measurement of the frequency of residual malignant cells. (Gray, et al., "Molecular cytogenetics in human cancer diagnosis," Cancer 1992; 69:1536–1542).

Other molecular markers for lung cancer include oncogenes and tumor suppressor genes. Dominant oncogenes are activated by mutation and lead to deregulated cellular growth. Such genes code for proteins that function as growth factors, growth factor receptors, signal transducing proteins and nuclear proteins involved in transcriptional regulation. Amplification, mutation, and translocations have been documented in many different cancer cells and have been shown to lead to gene activation or overexpression.

The ras family of oncogenes comprises a group of membrane associated GTP-binding proteins thought to be involved in signal transduction. Mutations within the ras oncogenes, resulting in sustained growth stimulation, have been identified in 15 to 30% of human NSCLC. (Birrer, et al., "Application of molecular genetics to the early diagnosis and screening of lung cancer," Cancer 1992; 52suppl; 2658s-2664s). Patients with tumors containing ras mutations had decreased survival compared with patients whose tumors had no ras mutations. Polymerase chain reaction (PCR) amplification of ras genes can be analyzed to determine the presence of mutations by several methods: (a) differential hybridization of $^{32}$P-labeled mutated oligonucleotides; (b) identification of new restriction enzyme sites created by the activating mutation; (c) single-strand conformational polymorphisms; and (d) nucleic acid sequencing. These methods combined with PCR technology could allow detection of an activated ras gene from sputum specimens.

Another family of dominant oncogenes, the erb B family, has been found to be abnormally expressed in lung cancer cells. This group codes for membrane-associated tyrosine kinase proteins and contains erb B1, the gene coding for the epidermal growth factor (EGF) receptor, and erb B2 (also called Her-2/neu). The erb B1 gene has been found to be amplified in NSCLC (up to 20% of squamous cell tumors), while the EGF receptor has been shown to be overexpressed in many NSCLC cells (approximately 90% of squamous cell tumors, 20 to 75% of adenocarcinomas, and rarely in large cell or undifferentiated tumors). (Birrer, et al., Cancer 1992:52 suppl; 2658s–2664s). Amplification of the related oncogene erb B2 (Her-2/neu) occurs infrequently in lung cancer but is a negative prognostic factor in breast cancer. However, overexpression of the erb B2 protein product, p185$^{neu}$, occurs in some NSCLC and may be related to poor prognosis. (Kern, et al., "p185$^{neu}$ expression in human lung adenocarcinomas predicts shortened survival," Cancer Res 1990; 50:5184–5191).

A third family of dominant oncogenes involved in lung cancer is the myc family. These genes encode nuclear phosphoproteins, which have potent effects on cell growth and which function as transcriptional regulators. Unlike ras genes, which are activated by point mutations in lung cancer cells, the myc genes are activated by overexpression of the cellular myc genes, either by gene amplification or by rearrangements, each ultimately leading to increased levels of myc protein. Amplification of the normal myc genes is seen frequently in SCLC and rarely in NSCLC.

The loss or inactivation of tumor suppressor genes may also be important steps in the pathway leading to invasive cancer. Tumor suppressor genes function normally to suppress cellular proliferation, and since they are recessive oncogenes, mutations or deletions must occur in both alleles of these genes before transformation occurs.

A phosphoprotein p53, which is encoded by a gene located on chromosome 17p, suppresses transformation in its wild-type state. While in its mutant state, p53 acts as a dominant oncogene. p53 functions in DNA binding and transcription activation. Mutations of p53 have been found in many human cancers including colon, breast, brain and lung cancer cells. (Birrer, et al., Cancer Res.(suppl) 1992, 52:2658s–2664s). In NSCLC cell lines, p53 mutations have been found at a rate of up to 74%. (Mitsudomi, et al., "p53 gene mutations in non-small-cell lung cancer cell lines and their correlation with the presence of ras mutations and clinical features," Oncogene 1992; 7:171–180).

Despite all of the advances made in the area of lung cancer, medical and surgical intervention has resulted in little change in the 5-year survival rate for lung cancer patients. Early detection holds the greatest hope for successful intervention. There remains a need for a practical method to diagnose lung cancer as close to its inception as possible. In order for early detection to be feasible, it is important that specific markers be found and their sequences elucidated.

A lung cancer marker antigen, specific for NSCLC, has now been found, sequenced, and cloned. The antigen is useful in methods for detection of non-small cell lung cancer and for potential production of antibodies and probes for treatment compositions.

BRIEF DESCRIPTION OF THE DRAWING

FIGURE 1 depicts the alignment of the amino acid sequence of HCAVIII with Previously described carbonic anhydrases. Conserved amino acids are shown in bold.

SUMMARY OF THE INVENTION

The invention concerns a lung cancer antigert (HCAVIII) gens specific for non-small cell lung cancer.

In one embodiment, the invention relates to an isolated substantially purified nucleic acid encoding the protein sequence shown in SEQ ID NO:2, and may be mRNA.

In other embodiments, the invention relates to cDNAs which encode a protein having a signal sequence (SEQ ID NO:2), or the mature form of the protein (SEQ ID NO:4), or a truncated form of the protein lacking the transmembrane domain (SEQ ID NO:10), or a protein in which one or more amino acids in the phosphorylation region of the protein have been altered to affect that function, an example of which is shown in SEQ ID NO:13.

In other embodiments, proteins encoded by the cDNA of SEQ ID NO:1, or SEQ ID NO:3 or SEQ ID NO:9, or a cDNA altered in the phosphorylation region, an example of which is SEQ ID NO:12, are provided.

In another aspect, the invention relates to a transcribable recombinant DNA clone for HCAVIII.

In further aspects of the invention, expression vectors for HCAVIII and modifications thereof are an object.

The invention further relates to methods of detection of lung cancer.

In one aspect an in situ hybridization technique is provided. In another aspect, a fluorescence in situ hybridization technique is provided. In a further aspect, an ELISA assay is provided. In another aspect, detection of carbonic anhydrase activity which correlates with lung cancer antigen is provided.

DETAILED DESCRIPTION OF THE INVENTION

The nucleic acid sequence coding for a cell surface protein (said protein hereinafter designated HCAVIII) which is highly specific for non-small cell lung cancer cells has now been obtained. This gene sequence will facilitate detection and treatment of the disease, which to date has often proven difficult.

The HCAVIII cDNA in the vector pLC56 has been sequenced and characterized including the entire coding region and substantially all of the upstream and downstream non-translated regions. The cDNA in pLC56 was sequenced on both strands from exonuclease III-generated deletions and subsequent subcloning into M13 vectors or directly from the cloning vectors using the di-deoxy method and a SEQUENASE® Version 2.0 kit (U.S. Biochemicals, Cleveland, Ohio). Additional regions of DNA were subcloned as small restriction fragments into the same vectors for sequence analysis. Overlapping segments were ordered using MacVector Align software (Kodak/IBI Technologies, New Haven Conn.). SEQ ID NO:1 represents the cDNA encoding HCAVIII and a presumed signal peptide. SEQ ID NO:2 represents the signal peptide (amino acid residues –29 to –1) followed by the mature protein (amino acid residues 1 to 325). As predicted from the cDNA sequence in pLC56, a protein of about 354 amino acids is encoded with the predictive size of 39448 daltons. A hydrophilicity plot (MacVector software, Kodak/IBI Technologies) of this protein provided strong evidence of a leader peptide at the N-terminus and a membrane-spanning segment near the C-terminus. The membrane-spanning segment provides evidence that this protein is membrane bound, as also predicted by its positive selection with panning methodology (See Watson, et al., Recombinant DNA, 2nd ed., pp. 115–116, 1992). The cleavage site of the signal as predicted by yon Heijne (yon Heijne, Gunnar, Nucleic Acids Res 1986; 14:4683–4690) is 29 amino acids down from the N-terminus methionine. SEQ ID NO:3 corresponds approximately to the coding region of the mature polypeptide. The subsequent "mature" protein is proposed to be 325 amino acids, initiating with serine, and of a calculated 36401 daltons and a pI of 6.42 (SEQ ID NO:4).

Homology searches against NCBI BlastN or BlastX version 1.3.12MP (National Center for Biotechnology Information, Bethesda, Md.) provided evidence that the gene and protein are novel, not previously identified in either database. (Altschul, et al., "Basic local alignment search tool," J Mol Biol 1990; 215:403–410). Additional searches against another database (Entrez, version 9) gave similar results. Alignment searches indicated this protein shares common features with the seven human carbonic anhydrase proteins previously identified. However, as described below, certain structural features distinct to HCAVIII exist that may confer unique properties to this protein and a possible role in the transformation pathway to tumorgenicity. This group of enzymes catalyze the hydration of carbon dioxide

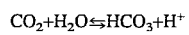

and in reverse the dehydration of $HCO_3^-$. This protein is identified as a carbonic anhydrase (CA) based on the conservation of amino acids at positions critical for the binding of $Zn^{+2}$, critical for the catalysis of $CO_2$, as well as numerous other conserved amino acids (see FIG. 1). The protein is 34 to 64 amino acids longer (at the C-terminus) than any previously reported carbonic anhydrase by virtue of the membrane-spanning region, also found in HCAIV and an additional approximate 30 amino acids on the cytoplasmic side of the cell, which are apparently missing in other human CA isoforms. In addition, this intracellular domain contains a phosphorylation site recognized by protein kinase C and other kinases, as defined by the motif "Arg—Arg—Lys—Ser" (SEQ ID NO:5 and SEQ ID NO:6) (amino acid residues 1–4 in SEQ ID NO:6 and amino acid residues 299–302 in SEQ ID NO:2 and SEQ ID NO:4). Interestingly, this motif is found only in HCAVIII, and at a functionally significant site, i.e., within the cytosol. A surface cleft essential for enzymatic function present on other carbonic anhydrases is conserved for this protein, suggesting this protein will confer enzymatic activity. HCAVI has been isolated from sheep salivary glands in a dimer conformation, by virtue of intermolecular disulfide bonds derived from cysteines at positions conserved in sheep and human HCAVI as well as the protein encoded by pLC56, but not other human CA's. Consequently, HCAVIII is likely presented on the cell surface as a dimer of a predicted 72804 daltons. In addition, five possible N-glycosylation sites are predicted by the primary amino acid sequence and the motif "Asn—Xaa—Ser (Thr)", beginning at amino acid residues −2, 51, 133, 151, and 202 in SEQ ID NO:2, respectively.

HCAVIII is expressed at a much higher level in a non-small cell lung cancer cell line (A549) than in normal lung tissue, other normal tissues, and other tumor cell lines which makes it useful in distinguishing this disease. This is clearly demonstrated in Table 1. Data for this table was obtained as follows. Total cellular RNA was isolated from the indicated actively growing cell lines as described by Chirgwin, et al., "Isolation of biologically active ribonucleic acid from sources enriched in ribonuclease," Biochemistry 1979; 18:5294–5299. RNA samples were fractionated over a 1% agarose-formaldehyde gel and transferred to a nylon membrane (Qiagen, Chatsworth, Calif.) by capillary action. The hybridization probe was generated from a 1 kilobase pair BstXI restriction fragment isolated from pLC56, a plasmid harboring the HCAVIII gene in its initial isolation. This fragment was radiolabeled with $^{32}$p using a PRIME-IT® Random Primer Labeling Kit obtained from Stratagene, La Jolla, Calif. A membrane containing RNA derived from healthy human tissue was purchased from Clonetech Laboratories, Inc., Palo Alto, Calif. RNA blots were hybridized in a standard cocktail containing $^{32}$P-labeled probe at 42° C. overnight then exposed to X-ray film. The same blots were subsequently, upon removal of the probe, rehybridized with a second $^{32}$P-labeled DNA from β-actin to serve as a positive control for integrity of the blotted RNA.

As shown in Table 1, normal lung tissue does not express the HCAVIII gene in detectable amounts. Other tumor cell lines fail to express, or express only in minor amounts, which will allow easy distinction of non-small cell carcinomas.

TABLE 1

NORTHERN BLOTS USING HCAVIII cDNA AGAINST NORMAL TISSUES AND TUMOR CELL LINES

| TISSUE | mRNA (kB) | INTENSITY |
| --- | --- | --- |
| NORMAL TISSUE | | |
| heart | nd[1] | — |
| brain | 4.5 | 1X[2] |
| placenta | 4.5 | 1X |
| lung | nd | — |
| liver | nd | — |
| skeletal muscle | nd | — |
| kidney | 4.5 | 100X |
| pancreas | 4.5 | 10X |
| TUMOR CELL LINE | | |
| A549 (lung carcinoma) | 3.5 | 5000X |
| | 5.4 | 50X |
| | 8.0 | 25X |
| | 9.0 | 25X |
| BT20 (breast carcinoma) | nd | — |
| G361 (melanoma) | nd | — |
| HT144 (melanoma) | nd | — |
| U937 (histiocytic lymphoma) | nd | — |
| KG-1 (myelogenous leukemia) | nd | — |

[1]nd = none detected
[2]1X = at limit of detection

In one embodiment of the invention, probes are made corresponding to sequences of the cDNA shown in SEQ ID NO:3, which are complimentary to the mRNA for HCAVIII. These probes can be radioactively or non-radioactively labeled in a number of ways well known to the art. The probes can be made of various lengths. Such factors as stringency and GC content may influence the desired probe length for particular applications. The probes correspond to a length of 10–986 nucleotides from SEQ ID NO:3. The labeled probes can then be bound to detect the presence or lack of mRNA encoding HCAVIII in biopsy material through in situ hybridization. The mRNA is expected to be associated with the presence of non-small cell tumors and to be a marker for the precancerous condition as well.

In situ hybridization provides a specificity to the target tissue that is not obtainable in Northern, PCR or other probe-driven technologies. In situ hybridization permits localization of signal in mixed-tissue specimens commonly found in most tumors and is compatible with many histologic staining procedures. This technique is comprised of three basic components: first is the preparation of the tissue sample provided by the pathologist to permit successful hybridization to the probe. Second is the preparation of the hybridization probe, typically a RNA complementary to the mRNA of the gene of interest (i.e., antisense RNA). RNA probes are preferred over DNA probes for in situ hybridizations mainly because background hybridization of the probe to irrelevant nucleic acids or nonspecific attachment to cell debris or subcellular organelles can be eliminated with RNAse treatment post-hybridization. Third is the hybridization and method of detection post-hybridization. Typically the RNA transcript probe has been radiolabeled by the incorporation of $^{32}$p or $^{35}$S nucleotides to permit subsequent detection of the probed specimen by autoradiography or quantitation of silver grains following treatment with autoradiographic emulsion. Nonradioactive detection systems have also been developed. In one example, biotinylated nucleotides can be substituted for the radioactive nucleotide in the RNA probe preparation, permitting visualization of the probed sample by immunocytochemistry-derived techniques. Example 1 describes in situ hybridization procedures using RNA probes derived from the HCAVIII gene, and Example 2 provides exemplary fluorescent in situ (FISH) hybridization procedures.

The cDNA for HCAVIII (SEQ ID NO:3) is currently in an expression vector which is be used to generate the protein in E. coli. This expression system described in Example 3 produces HCAVIII to be used as an antigen for the generation of antibodies (Example 4) for use in an ELISA assay to detect shed HCAVIII in body fluids as described in Example 5. The methods for production of antibodies and ELISA type assays are well known in the art. Exemplary methods and components of these procedures have been chosen and developed and are described in Examples 4 and 5.

The expression and purification of foreign proteins in *E. coli* is often problematic. On occasion, the protein is expressed at high levels but is deposited within the cell as an insoluble, denatured form termed an inclusion body. These bodies are often observed when the foreign protein contains a hydrophobic domain, such as found in the membrane spanning segment of HCAVIII. Through recombinant DNA technology, the DNA sequences encoding the membrane spanning segment of HCAVIII are deleted. The protein expressed in *E. coli* from this engineered plasmid is now in a soluble and native form within the cell, permitting a rapid and less harsh purification. In addition, the ELISA test to measure HCAVIII shed into body fluids as described in Example 5 relies on the recombinant protein produced from *E. coli*. Typically, the shed antigen is a membrane-bound receptor that has been released from the membrane spanning segment anchoring it to the cell. Consequently, the recombinant HCAVIII engineered to remove the membrane spanning segment is a more accurate representation of the putative HCAVIII shed antigen found in specimens and may prove to be the preferred antigen for polyclonal antisera and monoclonal antibody production as described for the development of an ELISA test. To produce the engineered plasmid, a first plasmid is constructed by cleaving pLC56 with the restriction enzyme Tth111 I, followed by treatment with $T_4$-DNA polymerase and dGTP, and finally with alkaline phosphatase to remove 5'-terminal phosphates. The DNA sample is then purified by phenol/chloroform extraction and ethanol precipitation. The sample is digested with the restriction endonuclease BspE1, then the fragments are resolved by agarose gel electrophoresis to permit the isolation of a 267 base pair fragment. A second plasmid described previously for expression of the HCAVIII mature protein (SEQ ID NO:4), is cleaved with EcoRI and BspE1 followed by alkaline phosphatase treatment and purification by phenol/chloroform extraction and ethanol precipitation. Two oligonucleotides are synthesized, being 5'-TGAGTCGACG (SEQ ID NO:7) and 5'-AATTCGTCGACTCA (SEQ ID NO:8), that complement each other and upon annealing, provide a termination codon (TGA) and sequence complementary to EcoRI cleaved DNA. Finally, the two oligonucleotides, the 267 base pair fragment, and the BspEI/EcoRI cleaved plasmid will be combined in a ligation reaction, and the resultant plasmid which contains the truncated DNA sequence (SEQ ID NO:9) are used to transform competent *E. coli*. Upon expression in *E. coli*, the resulting truncated protein (SEQ ID NO:10) is 271 amino acids and of a size consistent with other HCA's but lacking the membrane spanning segment and the intracellular domain.

An understanding of protein phosphorylation and its role in the mechanism of cell transformation has been actively pursued, most notably with tyrosine phosphorylation and oncogene activation. The role of serine/threonine protein phosphorylation by a variety of protein kinases including protein kinase C has been studied extensively with respect to signal transduction, but its role in oncogenesis is less clear. To provide a valuable tool to be used in the study of the role of HCAVIII serine phosphorylation in oncogenesis, an altered cDNA can be prepared to code for an altered protein. Changes to amino acids other than "Gly" may be realized by alterations of the oligonucleotide sequence (SEQ ID NO:11) to encode the selected residue. Other modifications to alter the serine phosphorylation site would utilize the described technology to modify either both "Arg" residues located within SEQ ID NO:6 or amino acid residues 299 and 300 of SEQ ID NO:4. Since "Arg" residues contain a net positive charge, the substituted amino acids would preferably be "Lys" or "His," also positively charged amino acids. An exemplary plasmid is produced in which the "Ser" codon (amino acid residue 4 of SEQ ID NO:6; amino acid residue 302 in SEQ ID NO:2 and SEQ ID NO:4), is converted to a "Gly" codon using an in vitro mutagenesis technique described in Example 3 and previously recited in Kunkel, Thomas, "Rapid and efficient site-specific mutagenesis without phenotypic selection," Proc Natl Acad Sci USA 1985; 82:488–492, and the oligonucleotide 5'-CTTTTTTGATAC-CCTTCCTTCTGAA (SEQ ID NO:11) (located in SEQ ID NO:1 at the base pairs 1010–1034 with 1022 as the mutagenized base pair). The DNA sequences containing the HCAVIII gene engineered for production of the mature protein and mutagenized codon is released from the mutagenesis vector by BamHI and EcoRI restriction endonucleases and ligated into pGEX4T1 cleaved with the same enzymes, and the resultant plasmid is used to transform competent *E. coli*. The codon mutagenesis is confirmed by DNA sequence analysis, and the protein is expressed and purified from *E. coli* as described in Example 3. The DNA sequence of the altered plasmid as shown in SEQ ID NO:12 differs from the gene encoding the mature protein (SEQ ID NO:2) in that the nucleotide 1022 (nucleotide 904 in SEQ ID NO:12) is changed from "A" to "G" and the protein sequence (SEQ ID NO:13) expressed by the altered plasmid is identical to the mature protein (SEQ ID NO:4) except that amino acid residue 302 is changed from "Ser" to "Gly."

Another way to detect the presence of increased HCAVIII could be to assay for levels of carbonic anhydrase activity in biopsy materials as described in Example 6. This should be a useful test as HCAVIII, although it is an immunologically unique molecule, contains small but distinct regions which are conserved between previously reported carbonic anhydrase proteins.

In another embodiment of the invention, primers are made complimentary to the HCAVIII cDNA (SEQ ID NO:3) for detecting expression of the gene. PCR amplification of cDNA from lung biopsy cells would indicate the presence of the same non-small cell lung carcinoma.

Due to the non-small cell lung cancer specificity of HCAVIII and the gene encoding the protein, antibodies specific for HCAVIII would also exhibit non-small cell lung cancer specificity which can be employed for diagnostic detection of HCAVIII in body fluids such as serum or urine or HCAVIII containing cells. Targeting of cancer therapeutic drugs to HCAVIII containing cells can also be developed using HCAVIII specific antibodies. The genetic expression of the gene encoding HCAVIII could be modulated by drugs or anti-sense technology resulting in an alteration of the cancer state of the HCAVIII containing cells.

Example 1

In Situ Hybridization Using RNA Probes Derived from the HCAVIII Gene

Tissue samples are treated with 4% paraformaldehyde (or an equivalent fixative), dehydrated in sequential ethanol solutions of increasing concentrations (e.g., 70%, 95% and 100%) with a final xylene incubation (see Current Protocols in Molecular Biology, pp. 14.01–14.3 and Immunocytochemistry II:IBRO Handbook Series: Methods in the Neurosciences Vol 14; pp 281–300, incorporated herein by reference). The tissue is embedded in molten paraffin, molded in a casting block and can be stored at room temperature. Tissue slices, typically 8 µm thick, are prepared with a microtome, dried onto gelatin-treated glass slides and stored at −20° C.

DNA sequences from the HCAVIII gene (SEQ ID NO:3) are subcloned into a plasmid engineered for production of RNA probes. In this example, a 776 bp DNA fragment is released from a pLC56 plasmid following BamHI/AccI digestion, where the BamHI site has been created by in vitro mutagenesis (see E. coli expression below). This fragment is ligated into pGEM-2 (Promega Biotec, Madison, Wis.) that was cleaved with BamHI and AccI and transformed into competent E. coli. This constructed plasmid contains the T7 RNA polymerase promoter downstream of the AccI restriction site and hence can drive transcription of the antisense HCAVIII sequences defined by the BamHI/AccI fragment. Following linearization of the subsequent plasmid with BamHI, an in vitro transcription reaction composed of transcription buffer (40 mM Tris-HCl, pH 7.5, 6 mMMgCl$_2$, 2 mM spermidine, 10 mM NaCl, 10 mM dithiothreitol, 1 u/ul ribonuclease inhibitor), linearized plasmid, 10 mM GTP, 10 mM ATP, 10 mM CTP, 100 µCi of ($^{35}$S)UTP, and T7 RNA polymerase is incubated at 37° C. Multiple RNA copies of the gene are produced that are used as a hybridization probe. The reaction is terminated by the addition of DNase, and the synthesized RNA is recovered from unincorporated nucleotides by phenol/chloroform extraction and sequential ethanol precipitations in the presence of 2.5M ammonium acetate.

The slides containing fixed, sectioned tissues are rehydrated in decreasing concentrations of ethanol (100%, 70% and 50%), followed by sequential treatments with 0.2N HCl, 2X SSC (where 20X SSC is 3M NaCl and 0.3M sodium citrate) at 70° C. to deparaffinate the sample, phosphate buffered saline (PBS), fixation in 4% paraformaldehyde and PBS wash. The slides are blocked to prevent nonspecific binding by the sequential additions of PBS/10 mM dithiothreitol (45° C.), 10 mM dithiothreitol/0.19% iodoacetamide/0.12% N-ethylmaleimide and PBS wash. The slides are equilibrated in 0.1M triethylamine, pH 8.0, followed by treatment in 0.1M triethylamine/0.25% acetic anhydride and 0.1M triethylamine/0.5% acetic anhydride and washed in 2X SSC. The slides are then dehydrated in increasing concentrations of ethanol (50%, 70% and 100%) and stored at −80° C.

A hybridization mix is prepared by combining 50% deionized formamide, 0.3M NaCl, 10 mM Tris-HCl, pH 8.0, 1 mM EDTA, 1X Denhardt's solution (0.02% Ficoll 400, 0.02% polyvinylpyrrolidone, 0.02% bovine serum albumin (BSA)), 500 µg/ml yeast tRNA, 500 µg/ml poly(A), 50 mM dithiothreitol, 10% polyethyleneglycol 6000 and the $^{35}$S-labeled RNA probe. This solution is placed on the fixed, blocked tissue slides which are then incubated at 45° C. in a moist chamber for 0.5 to 3 hours. The slides are washed to remove unbound probe in 50% formamide, 2X SSC, 20 mM 2-mercaptoethanol (55° C.), followed by 50% formamide, 2X SSC, 20 mM 2-mercaptoethanol and 0.5% Triton-X 100 (50° C.) and finally in 2X SSC/20 mM 2-mercaptoethanol (room temperature). The slides are treated with 10 mM Tris-HCl, pH 8.0/0.3M NaCl/40 µg/ml RNase A/2 µg/ml RNAse T1 (37° C.) to reduce levels of unbound RNA probe. Following RNAse treatment, the slides are washed in formamide/SSC buffers at 50° C., and room temperature and then dehydrated in increasing ethanol concentrations containing 0.3M ammonium acetate, and one final 100% ethanol wash. The slides are then exposed to X-ray film followed by emulsion autoradiography to detect silver grains.

Test tissue samples are compared to matched controls derived from normal lung tissue. Evidence of elevated transcription of the HCAVIII gens in test tissue compared to normal tissue, as determined by autoradiography (X-ray film) or alternatively by the quantitation of silver grains following emulsion autoradiography would provide evidence of a positive diagnosis for lung cancer.

Example 2

Fluorescent In Situ Hybridization (FISH) Using DNA Probes Derived from the HCAVIII Gene A genomic clone to the HCAVIII gens (SEQ ID NO:1) is isolated using a PCR primer pair which have been identified from the pLC56 cDNA sequence. This primer pair is located in putative exon 6 of the pLC56 gens, and they are identified as Probe Exon 6A (5'-ACATTGAAGAGCTGCTTCCGG-3'; SEQ ID NO:14) and Probe Exon 6B (5'-AATTTG-CACGGGGTTTCGG-3'; SEQ ID NO:15). The genomic clone of HCAVIII is then identified as a PCR product of about 119 bp using this primer pair from the designated genomic clone. This result is confirmed by Southern blotting and DNA sequence analysis.

The DNA probe comprising the genomic clone of HCAVIII plus flanking sequences is labeled in a random primer reaction with digoxigenin-11-dUTP (Boehringer Mannheim Biochemicals, Indianapolis, Ind.) by combining the DNA with dNTP(-TTP, final 0.05 mM), digoxigenin-11-dUTP/dTTP (0.0125 mM and 0.0375 mM, final), 10 mM 2-mercaptoethanol, 50 mM Tris-HCl, pH 7.5, 10 mMMgCl$_2$, 20 U of DNA polymerase I and 1 ng/ml DNase. The reaction is incubated at 15° C. for two hours, and then terminated by adding EDTA to a final concentration of 10 mM. The labeled DNA probe is further purified by gel filtration chromatography. It is apparent to those skilled in the art that other suitable substrates such as biotin-11-dUTP can be substituted for digoxigenin-11-dUTP in the procedure above.

A hybridization mix is prepared by combining 50% deionized formamide, 0.3M NaCl, 10 mMTris-HCl, pH 8.0, 1 mM EDTA, 1X Denhardt's solution (0.02% Ficoll 400, 0.02% polyvinylpyrrolidone, and 0.02% bovine serum albumin), 500 µg/ml yeast tRNA, 500 µg/ml poly(A), 50 mM dithiothreitol, 10% polyethyleneglycol 6000, and the labeled DNA probe.

Single cell suspensions of tissue biopsy material or normal tissue are fixed in methanol/glacial acetic acid (3:1 vol/vol) and dropped onto microscope slides. (Aanastasi, et al., "Detection of Trisomy 12 in chronic lymphocytic leukemia by fluorescent in situ hybridization to interphase cells: a simple and sensitive method," Blood 1992; 77:2456–2462). After the slides are heated for 1–2 hours at 60° C., the hybridization mix is applied to the slides which are then incubated at 45° C. in a moist chamber for 0.5–3 hours. After incubation, the slides are washed three times with a solution comprising 50% formamide and 2X SSC at 42° C., washed twice in 2X SSC at 42° C., and finally washed in 4X SSC at room temperature. The slide is blocked with a solution of 4X SSC and 1% BSA, and then washed with a solution of 4X SSC and 1% Triton X-100.

The hybridized digoxigenin-labeled probe is detected by adding a mixture of sheep anti-digoxigenin antibody (Boehringer Mannheim) diluted in 0.1M sodium phosphate, pH 8.0, 5% nonfat dry milk, and 0.02% sodium azide, followed by the addition of fluorescein-conjugated rabbit anti-sheep IG for detection. The slides are then washed in PBS, mounted in Vectashield (Vector Laboratories, Inc., Burlingame, Calif.), and viewed by fluorescent microscopy.

Hybridization signals are enumerated in tumor derived tissue and then compared to normal tissue. Normal tissue displays two distinct hybridization signal characteristics of a diploid state. Enumeration over the rate of two hybridization signals/cell is considered significant.

Example 3

Expression of HCAVIII

Expression of foreign proteins is often performed in *E. coli* when an immunogen or large amounts of protein are desired, as in the development of a diagnostic kit. A preferred system for *E. coli* expression has been described (Smith, et al., "Single-step purification of polypeptides expressed in *Escherichia coli* as fusions with glutathione-s-transferase," Gene 1988; 67:31–40) whereby glutathione transferase is expressed with amino acids representing the cloned protein of interest attached to the carboxylterminus. The fusion protein can then be purified via affinity chromatography and the protein of interest fused to glutathione transferase released by digestion with the protease thrombin or alternatively the fusion protein is released intact from the affinity column by competing levels of free glutathione.

To express the HCAVIII protein (SEQ ID NO:4) of this invention in *E. coli* using the above described technology, an expression plasmid was produced in which the glutathione transferase gene was fused in frame with the HCAVIII gene (SEQ ID NO:1) to produce a fusion protein. The fusion gene/expression plasmid was assembled from nucleic acids derived from the following sources. First, the expression plasmid pGEX4T1 (Pharmacia, Piscataway, N.J.) was cleaved in the polycloning region with the restriction endonucleases BamHI and EcoRI to permit insertion of the HCAVIII gene. Second, an oligonucleotide was synthesized, being 5'-GTCCACTTGGATCCGTTCACTGG-3' (SEQ ID NO:16). Using the in vitro mutagenesis procedure described by Kunkel (Proc Natl Acad Sci USA 1985; 82:488–492) and the above oligonucleotide, a BamHI restriction site was created without altering the amino acid codons of the original protein. In addition the created BamHI site was situated in correct reading frame and proximity to the predicted cleavage site separating the signal peptide from the mature protein. The DNA sequences encoding the mature protein were released from the mutagenesis vector as a BamHI/EcoRI fragment, where the EcoRI site originates from a polycloning region of the DNA sequencing vector pUC19 found downstream of the HCAVIII gene. The DNA fragments described above comprised of pGEX4T-1 cleaved at BamHI and EcoRI and the HCAVIII gene released as a BamHI/EcoRI fragment were combined in a mixture composed of 1X $T_4$ ligase buffer (50 mM Tris-HCl, 10 mMMgCl$_2$, 20 mM dithiothreitol, 1 mMATP, 50 µg/ml BSA, final pH 7.5) and $T_4$ DNA ligase (New England Biolabs, Beverly, Mass.). The ligated DNA was used to transform a suitable strain of *E. coli* such as XL-1 Blue (Stratagene). The recovered plasmid is sequenced to confirm the expected DNA sequence. Protein expression is induced in *E. coli* with the chemical isopropyl β-thiogalactoside, and the fusion protein is released by cell lysis, binding to an affinity column composed of glutathione-agarose (Sigma, St. Louis, Mo.) and cleavage with thrombin to release the HCAVIII protein.

The resulting protein is suitable as an immunogen for polyclonal or monoclonal antibody production and for usage in an ELISA kit as an internal standard and positive control.

The length of the resulting protein can be varied by altering the length of SEQ ID NO:1 prior to insertion into the expression plasmid, or by cleavage of amino acids from the protein resulting in the above example. Structure/function studies of other HCA's suggest modifications (as defined by deletions at the N-terminal and C-terminal) more extensive than disclosed in SEQ ID NO:9 would still permit the production and use of a protein as an immunogen or standard, these deletions being a protein defined by about amino acid residue 3 to amino acid residue 259 in SEQ ID NO:9. Using existing technology one could synthesize a peptide of approximately 10 to 40 amino acids in length that comprises a structural domain of HCAVIII. This synthesized peptide, coupled to a carrier protein, could be used for generating polyclonal antisera specific for native HCAVIII.

Example 4

Production of Antibodies to HCAVIII

The production of polyclonal antisera is described in great detail in Harlow, et al., Antibodies: A Laboratory Manual, Cold Spring Harbor Laboratories, New York, 1988 incorporated herein by reference. The HCAVIII protein (SEQ ID NO:4) in the presence of an adjuvant is injected into rabbits with a series of booster shots in a prescribed schedule optimal for high titers of antibody in serum.

An extensive description for producing monoclonal antibodies derived from the spleen B cells of an immunized mouse and an immortalized myeloma cell is found in the above reference for polyclonal antisera production. Mice are immunized with either the purified HCAVIII protein or a glutathione/HCAVIII fusion protein. Following cell fusion, selection for hybrid cells' and subcloning, hybridomas are screened for a positive antibody against whole A549 cells or purified HCAVIII protein using an indirect ELISA assay as described for the ELISA kit (see Example 5).

Example 5

ELISA Assay of Shed HCAVIII

An indirect ELISA screening assay for HCAVIII protein (SEQ ID NO:4) has been designed to detect and monitor the HCAVIII protein in body fluids including but not limited to serum and other biological fluids such as sputum or bronchial effluxion at effective levels necessary for sensitive but accurate determinations. It is intended to aid in the early diagnosis of non-small cell cancer, for which there currently is no effective treatment. An early-detection, accurate, non-invasive assay for non-small cell lung cancer would be of great benefit in the management of this disease.

The immunochemicals used in this procedure are rabbit anti-human HCAVIII antibody (purified IgG, IgM) which is produced according to the procedure given in Example 4, mouse anti-human HCAVIII (monoclonal) also produced according to the procedure given in Example 4, and goat anti-Rabbit IgG/peroxidase conjugate. The HCAVIII protein standard and internal positive control are produced as described in Example 3 for expression in *E. coli*.

Substrate components include 2M $H_2SO_4$ stored at room temperature; dimethylsulfoxide (Sigma Chemical Co., St. Louis, Mo.) stored at room temperature in a tightly capped bottle; 3',5,5'-tetramethylbenzidine (TMB) (Sigma Chemical Co.) used as a peroxidase substrate and stored at room temperature in the dark to prevent exposure to light; and hydrogen peroxide, 30%.

Several buffers, diluents, and blocking agents are used in the procedure. Note that no sodium azide preservative is used in any of the buffers. This is done to avoid any possible interference from the azide with the peroxidase conjugate.

Phosphate buffered saline (PBS) is prepared by adding 32.0 g sodium chloride, 0.8 g potassium phosphate, monobasic, 0.8 g potassium chloride, and 4.6 g sodium phosphate, dibasic, anhydrous, to 3.2 L deionized water and mixing to dissolve. After bringing the solution to 4 L with deionized water and mixing, the pH is adjusted to about 7.2. The buffer is stored at 4° C. for a maximum of 3 weeks.

The carbonate/bicarbonate coating buffer is prepared by mixing 1.45 g sodium carbonate and 7.25 g sodium bicarbonate in 800 ml deionized water until dissolved. The solution is brought to 1 L with deionized water and mixed, resulting in a pH of approximately 9.2. The buffer is stored at 4° C. for a maximum of 6 weeks.

Two bovine serum albumin solutions (BSA) are utilized as diluents. A 1% BSA solution in PBS, utilized as the second antibody/conjugate diluent, is prepared by adding 1 g BSA (bovine albumin, Fraction V, Sigma Chemical Co.) to 80 ml of PBS, allowing it to stand as it slowly goes into solution, adding PBS to a final volume of 100 ml, and then mixing. This diluent is stored at 4° C. for a maximum of 2 weeks; however if the solution becomes turbid, it is discarded. As a dilent for the standards and samples, a 0.025% BSA solution in PBS is prepared fresh for each assay by diluting the 1% BSA diluent with PBS 1:40 (vol/vol).

A 5% nonfat dry milk (NFDM) blocking agent is prepared fresh for each assay by adding 5 g nonfat dry milk to 100 ml PBS, mixing well to dissolve, and then vacuum filtering through Whatman #3 filter paper. The solution must be filtered to remove particulates prior to use in blocking. A 2.5% NFDM washing buffer is prepared fresh for each assay by diluting the 5% NFDM solution 1:1 (vol/vol) in PBS. Approximately 800 ml is required per assay plate.

The substrate buffer is 0.1M sodium acetate which is brought to a pH of 6.0 with 0.1M citric acid. This buffer is stored at 4° C. for a maximum of 6 weeks.

Immulon I REMOVAWELL strips (Dynatech, Chantilly, Va. #011-010-6301) (polystyrene support comprising 96 wells in an 8 row by 12 column format) are assembled in their holders. Antibody from Example 4 or equivalent is diluted to 25 µg/ml in room temperature coating buffer, and 200 µl is dispensed into each well. The plate is covered and stored overnight at room temperature.

1% BSA, PBS, and substrate buffer are brought to room temperature. 0.025% BSA, 5% NFDM and 2.5% NFDM are prepared fresh for each assay.

Microwells are aspirated with a 12 channel washer. The plate is inverted and blotted on a paper towel to expel residual well contents. 360 µl 5% NFDM is dispensed per well. The plate is covered and placed in a water-bath at 37° C. for 1 hour.

All samples are kept on ice after brief thawing at room temperature. The samples are vortexed, and the required aliquot is removed. Original samples are returned to freezer. If particulate matter is thought to be present, the aliquots of samples are spun in a microfuge and then placed in an ice bath. The samples and standard HCAVIII protein are diluted in 0.025% BSA/PBS. The appropriate dilution series are set up for standard and samples.

The assay plate is removed from the waterbath and each row of the wells is aspirated in turn. Each row of wells is then filled and aspirated in turn with the multiwell washer until the entire plate has been washed once.

Each well is aspirated and then filled with 2.5% NFDM. Each well is then aspirated and the plate blotted forcefully on a paper towel to expel residual well contents. The underside of the plate cover is dried.

Diluted samples and standards are added to the plate at 200 µl/well. The plate is covered and incubated in the 37° C. waterbath for 1 hour.

Rabbit anti-HCAVIII protein is diluted to 500 ng/ml in 1% BSA/PBS at room temperature. The assay plate is removed from the waterbath, samples aspirated and the plate is washed three times. The plate is blotted and 200 µl/well (100 ng/well) of antibody is dispensed. The plate is covered and incubated at 37° C. in the waterbath for 1 hour. Antibody dilution is discarded.

Goat anti-Rabbit IgG/Peroxidase conjugate is diluted to 1:32,000 in 1% BSA/PBS at room temperature. The assay plate is removed from the waterbath, aspirated, and washed three times. The plate is blotted, and the conjugate is dispensed at 200 µl/well. The plate is covered and incubated 1 hour at 37° C. Unused conjugate dilution is discarded.

Substrate mix is prepared 10–15 minutes prior to use by first dissolving TMB at a concentration of 10 mg/ml in DMSO. 29.85 ml substrate buffer is dispensed into a 50 ml centrifuge tube. 150 µl of TMB/DMSO is added and mixed thoroughly. Just prior to use, 50 µl of the substrate mix is discarded and the substrate mix volume is brought back to 30 ml by adding 50 µl 3% $H_2O_2$ (from a 30% stock diluted 1:10 (vol/vol) in substrate buffer). It is mixed thoroughly, and used immediately.

The plate is washed 2 times with 2.5% NFDM and blotted dry. The plate is rewashed 2 times with PBS and blotted dry. 200 µl/well TMB substrate mix is dispensed, the plate covered, and placed in the dark (drawer or covered box). It is incubated 30 minutes at room temperature. A separate well holder is prepared with one REMOVAWELL strip. 200 µl of substrate mix is dispensed into three wells, then 200 µl of deionized water is dispensed into another three wells. These are incubated along with the assay plate.

The peroxidase reaction is stopped by adding 50 µl/well 2M $H_2SO_4$ to all wells. The substrate color will shift from blue to yellow when stopped. If necessary, the well contents may be mixed with the 12 channel dispenser prior to reading the results. Acid can also be added to the six wells containing substrate and deionized water.

The plate is read with a microplate spectrophotometer reader.

Example 6

Carbonic Anhydrase (CA) Activity of Biopsy Tissue

Ice cold solutions of ITB (20 mM imidazole, 5 mM Tris, and 0.4 mMpara-nitrophenol, pH 9.4–9.9) and Buffer A (25 mM triethanolamine, 59 mM $H_2SO_4$, and 1 mM benzamidine HCl) are prepared.

A homogenate is prepared by scraping with a cell scraper into 1–2 ml of Buffer A a monolayer of tissue cells cultured from a tissue sample taken from a biopsy. A portion of the sample is then boiled to inactivate CA.

A tube is placed in an ice water bath. For the macroassay, a 10×75 mm glass tubes and rubber stopper with 16 gauge and 18 gauge needle ports is used; for the microassay, a 6×50 mm glass tube and rubber stopper with 18 gauge needle port and 20 gauge needle with attached PE90 tubing is used. The sample is added along with ice cold water to a final volume of 500 μl for the macroassay or 50 μl for the microassay. 500 μl (macro) or 50 μl (micro) ice cold water is used for a water control. 10 μl antifoam (A. H. Thomas, Philadelphia, Pa.) is added to the tube which is then incubated in ice water for 0.5 to 3 minutes.

The tube is capped with a stopper and $CO_2$ at 150 ml/min (macro) or 100 ml/min (micro) is bubbled through the smaller needle port for 30 sec.

50 μl (macro) or 50 μl (micro) of the ITB solution is rapidly added through the larger needle port with a cold Hamilton syringe. The sample becomes yellow.

Using a timer or stopwatch, the time at which the solution in the tube becomes colorless is measured and recorded. The tube may be momentarily removed from the bath and held in front of a white background to determine the color change. Comparison to a previously acidified sample may be used.

The procedure is repeated with the boiled sample. The volume of sample that corresponds to approximately one enzyme unit is determined using the formula below.

Volume (1EU)=VEU=volume used×log2×log (boiled time/ activated time) One enzyme unit is the activity that halves the boiled control time.

The assay is repeated 1–3 times with the sample and boiled sample, using the adjusted volume of sample.

We claim:

1. An isolated nucleic acid comprising a nucleotide sequence encoding the amino acid sequence depicted in SEQ ID NO:2.

2. The nucleic acid according to claim 1 wherein said an isolated nucleic acid is mRNA.

3. An isolated cDNA encoding the protein of SEQ ID NO:2.

4. The isolated cDNA of claim 3, comprising the coding sequence of SEQ ID NO:1.

5. An isolated cDNA encoding the protein of SEQ ID NO:4.

6. The isolated cDNA of claim 5, comprising the coding sequence of SEQ ID NO:3.

7. An isolated cDNA encoding the protein of SEQ ID NO:10.

8. The isolated cDNA of claim 7, comprising the coding sequence of SEQ ID NO:9.

9. An isolated cDNA comprising a nucleotide sequence encoding the amino acid sequence depicted in SEQ ID NO:4 except amino acid residue 30 is a single amino acid residue other than Ser.

10. The isolated cDNA of claim 9, comprising the coding sequence of SEQ ID NO:12.

11. An isolated cDNA encoding human carbonic anhydrase VIII of a 1.1 kilobase transcript isolated from human A549 cells.

12. An expression vector comprising the coding region of the sequence depicted in SEQ ID NO: 1.

13. An expression vector comprising the coding region of the sequence depicted in SEQ ID NO:3.

14. An expression vector comprising the coding region the sequence depicted in SEQ ID NO:9.

15. An expression vector comprising the coding region of the sequence depicted in SEQ ID NO: 12.

* * * * *

UNITED STATES PATENT AND TRADEMARK OFFICE
CERTIFICATE OF CORRECTION

PATENT NO : 5,589,579

DATED : December 31, 1996

INVENTOR(S) : Richard M. Torczynski, et al.

It is certified that error appears in the above-identified patent and that said Letters Patent are hereby corrected as shown below:

Col. 1, line 41, after "1986", delete ")".

Col. 2, line 30, after "NSCLC", change "Mab" to "MAb".

Col. 2, line 46, after "8)", change "," to ".".

Col. 2, line 55, after "73:", change "1369" to "1368".

Col. 3, line 37, after "and", change "NCAmRNA" to "NCA mRNA".

Col. 3, line 38, before "or", change "NCAmRNA" to "NCA mRNA".

Col. 3, line 38, after "mRNA.", change "CEA-relatedmRNA" to "CEA-related mRNA".

Col. 3, line 39, after "by", change "NCAmRNA" to "NCA mRNA".

Col. 3, line 40, after "of", change "CEAmRNA" to "CEA mRNA".

Col. 5, line 35, after "with", change "Previously" to "previously".

Col. 7, line 2, after "HCAIV", insert --,--.

Col. 7, line 29, after "table", change "was" to "were".

Col. 7, line 40, after "with", change "$^{32}p$" to "$^{32}P$".

Col. 8, line 53, after "of", change "$^{32}p$" to "$^{32}P$".

Col. 11, line 23, before "ribonuclease", change "u/ul" to "U/µl".

Col. 13, line 24, after "the", change "carboxylterminus" to "carboxyl-terminus".

Col. 13, line 46, after "In addition", insert --,--.

Col. 14, line 37, after "cells", delete " ' ".

Col. 16, line 61, after "0.4", change "mMpara-nitrophenol" to "mM para-nitrophenol".

UNITED STATES PATENT AND TRADEMARK OFFICE
CERTIFICATE OF CORRECTION

PATENT NO. : 5,589,579
DATED : December 31, 1996
INVENTOR(S) : Richard M. Torczynski, et al.

It is certified that error appears in the above-identified patent and that said Letters Patent is hereby corrected as shown below:

Col. 17, line 2, after "glass", change "tubes" to "tube".

Col. 38, Claim 9, line 59, before "is", change "30" to "302".

Signed and Sealed this

Seventeenth Day of April, 2001

Attest:

NICHOLAS P. GODICI

Attesting Officer    Acting Director of the United States Patent and Trademark Office